United States Patent
Ashrafi et al.

(10) Patent No.: US 10,048,202 B2
(45) Date of Patent: *Aug. 14, 2018

(54) SYSTEM AND METHOD FOR DETECTION OF MATERIALS USING ORBITAL ANGULAR MOMENTUM SIGNATURES

(71) Applicant: NxGen Partners IP, LLC, Dallas, TX (US)

(72) Inventors: Solyman Ashrafi, Plano, TX (US); Roger D. Linquist, Dallas, TX (US)

(73) Assignee: NxGen Partners IP, LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/677,552

(22) Filed: Aug. 15, 2017

(65) Prior Publication Data

US 2017/0370838 A1 Dec. 28, 2017

Related U.S. Application Data

(63) Continuation of application No. 15/398,857, filed on Jan. 5, 2017, now Pat. No. 9,810,628, which is a
(Continued)

(51) Int. Cl.
*G01N 21/59* (2006.01)
*G01N 21/17* (2006.01)
*A61B 5/1455* (2006.01)
*G01N 33/483* (2006.01)
*A61B 5/145* (2006.01)
(Continued)

(52) U.S. Cl.
CPC ............ *G01N 21/59* (2013.01); *A61B 5/1455* (2013.01); *A61B 5/14532* (2013.01); *G01N 21/17* (2013.01); *G01N 21/21* (2013.01); *G01N 33/483* (2013.01); *G01N 33/487* (2013.01);
(Continued)

(58) Field of Classification Search
CPC ........ G01N 21/17; G01N 21/21; G01N 21/59; G01N 33/483; G01N 33/4833; G01N 33/487; G01N 2021/1765; G01N 2021/178; G01N 24/00; A61B 5/1455;
(Continued)

(56) References Cited

U.S. PATENT DOCUMENTS 3,459,466 A 8/1969 Giordmaine
3,614,722 A 10/1971 Jones
(Continued)

OTHER PUBLICATIONS

Speirits, Fiona C. et al. "Do Waves Carrying Orbital Angular Momentum Possess Azimuthal Linear Momentum?" 2013, Physical Review Letters 111, pp. 103602-1 to 103602-3.*
(Continued)

*Primary Examiner* — Gordon J Stock, Jr.
(74) *Attorney, Agent, or Firm* — Gregory M. Howison

(57) ABSTRACT

An apparatus for identifying a material within a sample comprising signal generation circuitry generates a first signal including a first orbital angular momentum (OAM) signature and applies the first signal to the sample. A detector receives the first signal after the first signal passes through the sample and identifies the material within the sample based on a detected second orbital angular momentum caused by an interaction of the first signal with chiral molecules within the sample.

20 Claims, 30 Drawing Sheets

Related U.S. Application Data continuation of application No. 14/942,641, filed on Nov. 16, 2015, now Pat. No. 9,575,001, and a continuation-in-part of application No. 14/339,836, filed on Jul. 24, 2014, now Pat. No. 9,267,877, and a continuation-in-part of application No. 14/875,507, filed on Oct. 5, 2015, now Pat. No. 9,784,724.

(60) Provisional application No. 62/081,846, filed on Nov. 19, 2014.

(51) Int. Cl.
    G01N 33/487    (2006.01)
    G01N 24/00     (2006.01)
    G01N 21/21     (2006.01)

(52) U.S. Cl.
    CPC ......... *G01N 33/4833* (2013.01); *G01N 24/00* (2013.01); *G01N 2021/1765* (2013.01)

(58) Field of Classification Search
    CPC ............ A61B 5/14532; G01R 33/3657; G01R 33/3692; G01R 33/4833
    See application file for complete search history.

(56) References Cited

U.S. PATENT DOCUMENTS

| | | | |
|---|---|---|---|
| 4,379,409 | A | 4/1983 | Primbsch et al. |
| 4,503,336 | A | 3/1985 | Hutchin et al. |
| 4,736,463 | A | 4/1988 | Chavez |
| 4,862,115 | A | 8/1989 | Lee et al. |
| 5,051,754 | A | 9/1991 | Newberg |
| 5,220,163 | A | 6/1993 | Toughlian et al. |
| 5,222,071 | A | 6/1993 | Pezeshki et al. |
| 5,272,484 | A | 12/1993 | Labaar |
| 5,543,805 | A | 8/1996 | Thaniyavarn |
| 5,555,530 | A | 9/1996 | Meehan |
| 6,337,659 | B1 | 1/2002 | Kim |
| 6,992,829 | B1 | 1/2006 | Jennings et al. |
| 7,577,165 | B1 | 8/2009 | Barrett |
| 7,729,572 | B1 | 6/2010 | Pepper et al. |
| 7,792,431 | B2 | 9/2010 | Jennings et al. |
| 8,432,884 | B1 | 4/2013 | Ashrafi |
| 8,503,546 | B1 | 8/2013 | Ashrafi |
| 8,559,823 | B2 | 10/2013 | Izadpanah et al. |
| 8,811,366 | B2 | 8/2014 | Ashrafi |
| 9,077,577 | B1 | 7/2015 | Ashrafi |
| 9,784,724 | B2 * | 10/2017 | Ashrafi ............... G01N 33/487 |
| 2005/0254826 | A1 | 11/2005 | Jennings et al. |
| 2005/0259914 | A1 | 11/2005 | Padgett et al. |
| 2010/0013696 | A1 | 1/2010 | Schmitt et al. |
| 2012/0207470 | A1 | 8/2012 | Djordevic et al. |
| 2013/0027774 | A1 | 1/2013 | Bovino et al. |
| 2013/0235744 | A1 | 9/2013 | Chen et al. |
| 2014/0355624 | A1 | 12/2014 | Li et al. |
| 2015/0098697 | A1 | 4/2015 | Marom et al. |

OTHER PUBLICATIONS

Vasnetsov, M. V., Pasko, V.A. & Soskin, M.S.; Analysis of orbital angular momentum of a misaligned optical beam; New Journal of Physics 7, 46 (2005).

Byun, S.H., Haji, G.A. & Young, L.E.; Development and application of GPS signal multipath simulator; Radio Science, vol. 37, No. 6, 1098 (2002).

Tamburini, Fabrizio; Encoding many channels on the same frequency through radio vorticity: first experimental test; New Journal of Physics 14, 033001 (2012).

Gibson, G. et al., Free-space information transfer using light beans carrying orbital angular momentum; Optical Express 12, 5448-5456 (2004).

Yan, Y. et al.; High-capacity millimetre-wave communications with orbital angular momentum multiplexing; Nature Communications; 5, 4876 (2014).

Hur, Sooyoung et at.; Millimeter Wave Beamforming for Wireless Backhaul and Access in Small Cell Networks. IEEE Transactions on Communications, vol. 61, 4391-4402 (2013).

Allen, L., Beijersbergen, M., Spreeuw, R.J.C., and Woerdman, J.P.; Orbital Angular Momentum of Light and the Transformation of Laguerre-Gaussian Laser Modes; Physical Review A, vol. 45, No. 11; 8185-8189 (1992).

Anderson, Jorgen Bach; Rappaport, Theodore S.; Yoshida, Susumu; Propagation Measurements and Models for Wireless Communications Channels; 33 42-49 (1995).

Iskander, Magdy F.; Propagation Prediction Models for Wireless Communication Systems; IEEE Transactions on Microwave Theory and Techniques, vol. 50., No. 3, 662-673 (2002).

Wang, Jian, et al.; Terabit free-space data transmission employing orbital angular momentum multiplexing. Nature Photonics; 6, 488-496 (2012).

Katayama, Y., et al.; Wireless Data Center Networking with Steered-Beam mmWave Links; IEEE Wireless Communication Network Conference; 2011, 2179-2184 (2011).

Molina-Terriza, G., et al.; Management of the Angular Momentum of Light: Preparation of Photons in Multidimensional Vector States of Angular Momentum; Physical Review Letters; vol. 88, No. 1; 77, 013601/1-4 (2002).

Rapport, T.S.; Millimeter Wave Mobile Communications for 5G Cellular: It Will Work!; IEEE Access, 1, 335-349 (2013).

Solyman Ashrafi, Channeling Radiation of Electrons in Crystal Lattices, Essays on Classical and Quantum Dynamics, Gordon and Breach Science Publishers, 1991.

Solyman Ashrafi, Solar Flux Forecasting Using Mutual Information with an Optimal Delay, Advances in the Astronautical Sciences, American Astronautical Society, vol. 84 Part II, 1993.

Solyman Ashrafi, PCS system design issues in the presence of microwave OFS, Electromagnetic Wave Interactions, Series on Stability, Vibration and Control of Systems, World Scientific, Jan. 1996.

Solyman Ashrafi, Performance Metrics and Design Parameters for an FSO Communications Link Based on Multiplexing of Multiple Orbital-Angular-Momentum Beams, IEEE Globecom 2014, paper 1570005079, Austin, TX, Dec. 2014(IEEE, Piscataway, NJ, 2014).

Solyman Ashrafi, Optical Communications Using Orbital Angular Momentum Beams, Adv. Opt. Photon. 7, 66-106, Advances in Optics and Photonic, 2015.

Solyman Ashrafi, Performance Enhancement of an Orbital-Angular-Momentum based Free-space Optical Communications Link Through Beam Divergence Controlling, IEEE/OSA Conference on Optical Fiber Communications (OFC) and National Fiber Optics Engineers Conference (NFOEC),paper M2F.6, Los Angeles, CA, Mar. 2015 (Optical Society of America, Washington, D.C., 2015).

Solyman Ashrafi, Experimental demonstration of enhanced spectral efficiency of 1.18 symbols/s/Hz using multiple-layer-overlay modulation for QPSK over a 14-km fiber link. OSA Technical Digest (online), paper JTh2A.63. The Optical Society, 2014.

Solyman Ashrafi, Link Analysis of Using Hermite-Gaussian Modes for Transmitting Multiple Channels in a Free-Space Optical Communication System, The Optical Society, vol. 2, No. 4, Apr. 2015.

Solyman Ashrafi, Performance Metrics and Design Considerations for a Free-Space Optical Orbital-Angular-Momentum Multiplexed Communication Link, The Optical Society, vol. 2, No. 4, Apr. 2015.

Solyman Ashrafi, Demonstration of Distance Emulation for an Orbital-Angular-Momentum Beam. OSA Technical Digest (online), paper STh1F.6. The Optical Society, 2015.

Solyman Ashrafi, Free-Space Optical Communications Using Orbital-Angular-Momentum Multiplexing Combined with MIMO-Based Spatial Multiplexing. Optics Letters, vol. 40, No. 18, Sep. 4, 2015.

Solyman Ashrafi, Enhanced Spectral Efficiency of 2.36 bits/s/Hz Using Multiple Layer Overlay Modulation for QPSK over a 14-km Single Mode Fiber Link. OSA Technical Digest (online), paper SW1M.6. The Optical Society, 2015.

(56) References Cited

OTHER PUBLICATIONS

Solyman Ashrafi, Experimental Demonstration of a 400-Gbit/s Free Space Optical Link Using Multiple Orbital-Angular-Momentum Beams with Higher Order Radial Indices. OSA Technical Digest (online), paper SW4M.5. The Optical Society, 2015.
Solyman Ashrafi, Experimental Demonstration of 16-Gbit/s Millimeter-Wave Communications Link using Thin Metamaterial Plates to Generate Data-Carrying Orbital-Angular-Momentum Beams, ICC 2015, London, UK, 2014.
Solyman Ashrafi, Experimental Demonstration of Using Multi-Layer-Overlay Technique for Increasing Spectral Efficiency to 1.18 bits/s/Hz in a 3 Gbit/s Signal over 4-km Multimode Fiber. OSA Technical Digest (online), paper JTh2A.63. The Optical Society, 2015.
Solyman Ashrafi, Experimental Measurements of Multipath-Induced Intra- and Inter-Channel Crosstalk Effects in a Millimeter-wave Communications Link using Orbital-Angular-Momentum Multiplexing, IEEE International Communication Conference(ICC) 2015, paper1570038347, London, UK, Jun. 2015(IEEE, Piscataway, NJ, 2015).
Solyman Ashrafi, Performance Metrics for a Free-Space Communication Link Based on Multiplexing of Multiple Orbital Angular Momentum Beams with Higher Order Radial Indice. OSA Technical Digest (online), paper JTh2A.62. The Optical Society, 2015.
Solyman Ashrafi, 400-Gbit/s Free Space Optical Communications Link Over 120-meter using Multiplexing of 4 Collocated Orbital-Angular-Momentum Beams, IEEE/OSA Conference on Optical Fiber Communications (OFC) and National Fiber Optics Engineers Conference (NFOEC),paper M2F.1, Los Angeles, CA, Mar. 2015 (Optical Society of America, Washington, D.C., 2015).
Solyman Ashrafi, Experimental Demonstration of Two-Mode 16-Gbit/s Free-Space mm-Wave Communications Link Using Thin Metamaterial Plates to Generate Orbital Angular Momentum Beams, Optica, vol. 1, No. 6, Dec. 2014.
Solyman Ashrafi, Demonstration of an Obstruction-Tolerant Millimeter-Wave Free-Space Communications Link of Two 1-Gbaud 16-QAM Channels using Bessel Beams Containing Orbital Angular Momentum, Third International Conference on Optical Angular Momentum (ICOAM), Aug. 4-7, 2015, New York USA.
Solyman Ashrafi, An Information Theoretic Framework to Increase Spectral Efficiency, IEEE Transactions on Information Theory, vol. XX, No. Y, Oct. 2014, Dallas, Texas.
Solyman Ashrafi, Acoustically induced stresses in elastic cylinders and their visualization, The Journal of the Acoustical Society of America 82(4):1378-1385, Sep. 1987.
Solyman Ashrafi, Splitting of channeling-radiation peaks in strained-layer superlattices, Journal of the Optical Society of America B 8(12), Nov. 1991.
Solyman Ashrafi, Experimental Characterization of a 400 Gbit/s Orbital Angular Momentum Multiplexed Free-space Optical Link over 120-meters, Optics Letters, vol. 41, No. 3, pp. 622-625, 2016.
Solyman Ashrafi, Orbital-Angular-Momentum-Multiplexed Free-Space Optical Communication Link Using Transmitter Lenses, Applied Optics, vol. 55, No. 8, pp. 2098-2103, 2016.
Solyman Ashrafi, 32 Gbit/s 60 GHz Millimeter-Wave Wireless Communications using Orbital-Angular-Momentum and Polarization Mulitplexing, IEEE International Communication Conference (ICC) 2016, paper 1570226040, Kuala Lumpur, Malaysia, May 2016 (IEEE, Piscataway, NJ, 2016).
Solyman Ashrafi, Tunable Generation and Angular Steering of a Millimeter-Wave Orbital-Angular-Momentum Beam using Differential Time Delays in a Circular Antenna Array, IEEE International Communication Conference (ICC) 2016, paper 1570225424, Kuala Lumpur, Malaysia, May 2016 (IEEE, Piscataway, NJ, 2016).
Solyman Ashrafi, A Dual-Channel 60 GHz Communications Link Using Patch Antenna Arrays to Generate Data-Carrying Orbital-Angular-Momentum Beams, IEEE International Communication Conference (ICC) 2016, paper 1570224643, Kuala Lumpur, Malaysia, May 2016 (IEEE, Piscataway, NJ, 2016).

Solyman Ashrafi, Demonstration of OAM-based MIMO FSO link using spatial diversity and MIMO equalization for turbulence mitigation, IEEE/OSA Conference on Optical Fiber Communications (OFC), paper Th1H.2, Anaheim, CA, Mar. 2016 (Optical Society of America, Washington, D.C., 2016).
Solyman Ashrafi, Dividing and Multiplying the Mode Order for Orbital-Angular-Momentum Beams, European Conference on Optical Communications (ECOC), paper Th.4.5.1, Valencia, Spain, Sep. 2015.
Solyman Ashrafi, Exploiting the Unique Intensity Gradient of an Orbital-Angular-Momentum Beam for Accurate Receiver Alignment Monitoring in a Free-Space Communication Link, European Conference on Optical Communications (ECOC), paper We.3.6.2, Valencia, Spain, Sep. 2015.
Solyman Ashrafi, Experimental Demonstration of a 400-Gbit/s Free Space Optical Link using Multiple Orbital-Angular-Momentum Beams with Higher Order Radial Indices, APS/IEEE/OSA Conference on Lasers and Electro-Optics (CLEO), paper SW4M.5, San Jose, CA, May 2015 (OSA, Wash., D.C., 2015).
Solyman Ashrafi, Spurious Resonances and Modelling of Composite Resonators, 37th Annual Symposium on Frequency Control, 1983.
Solyman Ashrafi, Splitting and contrary motion of coherent bremsstrahlung peaks in strained-layer superlattices, Journal of Applied Physics 70:4190-4193, Dec. 1990.
Solyman Ashrafi, Nonlinear Techniques for Forecasting Solar Activity Directly From its Time Series, Proceedings of Flight Mechanics/Estimation Theory Symposium, National Aeronautics and Space Administration, May 1992.
Solyman Ashrafi, Demonstration of using Passive Integrated Phase Masks to Generate Orbital-Angular-Momentum Beams in a Communications Link, APS/IEEE/OSA Conference on Lasers and Electro-Optics (CLEO), paper 2480002, San Jose, CA, Jun. 2016 (OSA, Wash., D.C., 2016).
Solyman Ashrafi, Combining Schatten's Solar Activity Prediction Model with a Chaotic Prediction Model, National Aeronautics and Space Administration, Nov. 1991.
Solyman Ashrafi, Detecting and Disentangling Nonlinear Structure from Solar Flux Time Series, 43rd Congress of the International Astronautical Federation, Aug. 1992.
Solyman Ashrafi, Physical Phaseplate for the Generation of a Millimeter-Wave Hermite-Gaussian Beam, IEEE Antennas and Wireless Propagation Letters, RWS 2016; pp. 234-237.
Solyman Ashrafi, Future Mission Studies: Forecasting Solar Flux Directly From Its Chaotic Time Series, Computer Sciences Corp., Dec. 1991.
Solyman Ashrafi, CMA Equalization for a 2 Gb/s Orbital Angular Momentum Multiplexed Optical Underwater Link through Thermally Induced Refractive Index Inhomogeneity, APS/IEEE/OSA Conference on Lasers and Electro-Optics (CLEO), paper 2479987, San Jose, CA, Jun. 2016 (OSA, Wash., D.C., 2016).
Solyman Ashrafi, 4 Gbit/s Underwater Transmission Using OAM Multiplexing and Directly Modulated Green Laser, APS/IEEE/OSA Conference on Lasers and Electro-Optics (CLEO), paper 2477374, San Jose, CA, Jun. 2016 (OSA, Wash., D.C., 2016).
Solyman Ashrafi, Evidence of Chaotic Pattern in Solar Flux Through a Reproducible Sequence of Period-Doubling-Type Bifurcations; Computer Sciences Corporation (CSC); Flight Mechanics/Estimation Theory Symposium; NASA Goddard Space Flight Center; Greenbelt, Maryland; May 21-23, 1991.
Solyman Ashrafi; Future Mission Studies: Preliminary Comparisons of Solar Flux Models; NASA Goddard Space Flight Center Flight Dynamics Division; Flight Dynamics Division Code 550; Greenbelt, Maryland; Dec. 1991.
H. Yao et al.; Patch Antenna Array for the Generation of Millimeter-wave Hermite-Gaussian Beams, IEEE Antennas and Wireless Propagation Letters; 2016.
Yongxiong Ren et al.; Experimental Investigation of Data Transmission Over a Graded-index Multimode Fiber Using the Basis of Orbital Angular Momentum Modes.
Ren, Y. et al.; Experimental Demonstration of 16 Gbit/s millimeter-wave Communications using MIMO Processing of 2 OAM Modes

(56) References Cited

OTHER PUBLICATIONS on Each of Two Transmitter/Receiver Antenna Apertures. In Proc. IEEE GLobal TElecom. Conf. 3821-3826 (2014).

Li, X. et al.; Investigation of interference in multiple-input multiple-output wireless transmission at W band for an optical wireless integration system. Optics Letters 38, 742-744 (2013).

Padgett, Miles J. et al., Divergence of an orbital-angular-momentum-carrying beam upon propagation. New Journal of Physics 17, 023011 (2015).

Mahmouli, F.E. & Walker, D. 4-Gbps Uncompressed Video Transmission over a 60-GHz Orbital Angular Momentum Wireless Channel. IEEE Wireless Communications Letters, vol. 2, No. 2, 223-226 (Apr. 2013).

* cited by examiner

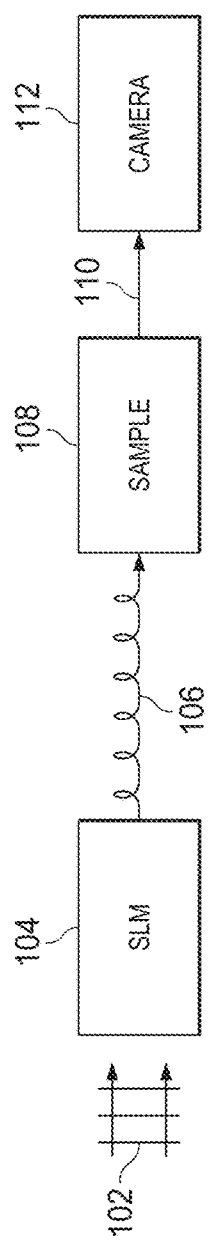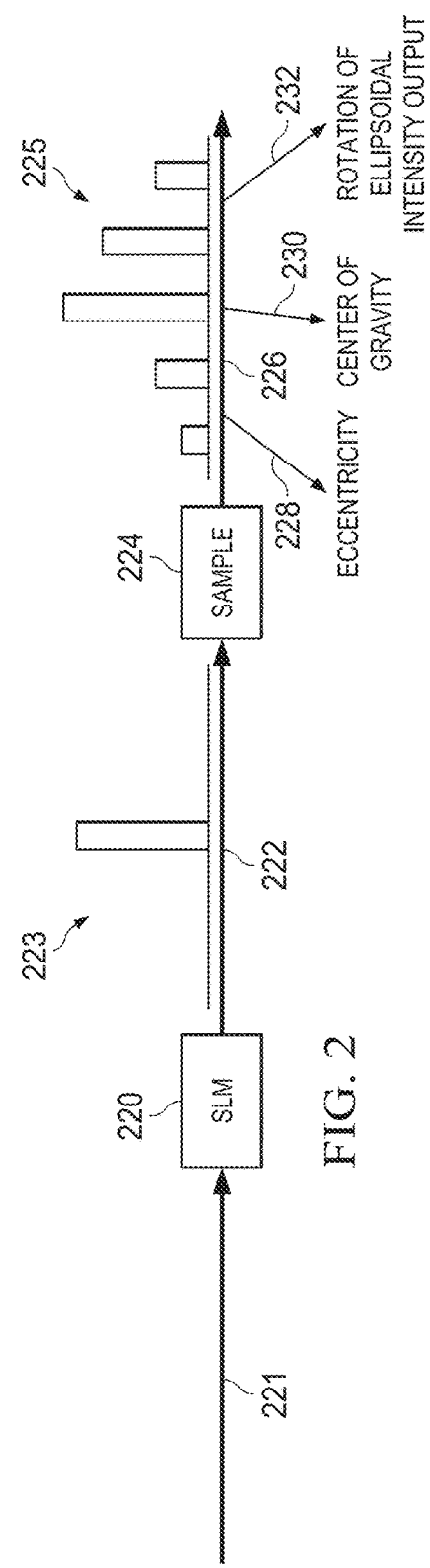

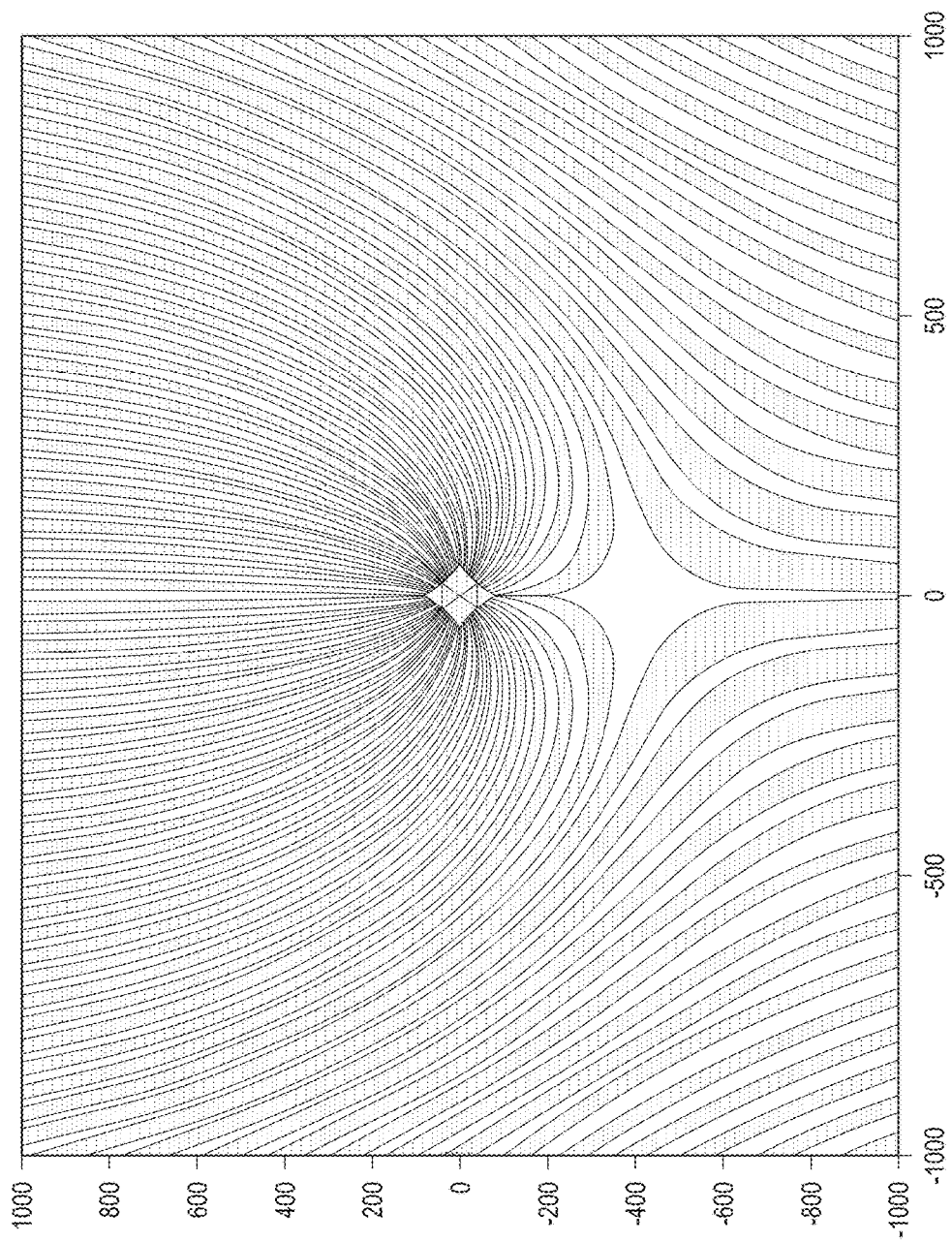

WATER

15% GLUCOSE IN WATER

WATER

15% GLUCOSE IN WATER

AMPLITUDE

PHASE

SYSTEM AND METHOD FOR DETECTION OF MATERIALS USING ORBITAL ANGULAR MOMENTUM SIGNATURES

CROSS-REFERENCE TO RELATED APPLICATIONS

This application is a continuation of U.S. patent application Ser. No. 15/398,857, filed Jan. 5, 2017, entitled SYSTEM AND METHOD FOR DETECTION OF MATERIALS USING ORBITAL ANGULAR MOMENTUM SIGNATURES, which is a continuation of U.S. patent application Ser. No. 14/942,641, filed Nov. 16, 2015, entitled SYSTEM AND METHOD FOR DETECTION OF MATERIALS USING ORBITAL ANGULAR MOMENTUM SIGNATURES, now U.S. Pat. No. 9,575,001, issued Feb. 21, 2017, which claims benefit of U.S. Provisional Application No. 62/081,846, filed on Nov. 19, 2014, entitled DISTINCT SIGNATURES FOR CONCENTRATION MEASUREMENTS, the specifications of which are incorporated by reference herein in their entirety.

U.S. application Ser. No. 14/942,641 is also a Continuation-in-Part of U.S. application Ser. No. 14/875,507, filed on Oct. 5, 2015, entitled SYSTEM AND METHOD FOR EARLY DETECTION OF ALZHEIMERS BY DETECTING AMYLOID-BETA USING ORBITAL ANGULAR MOMENTUM. U.S. application Ser. No. 14/942,641 is also a Continuation-in-Part of U.S. application Ser. No. 14/339,836, filed on Jul. 24, 2014, entitled SYSTEM AND METHOD FOR MAKING CONCENTRATION MEASUREMENTS WITHIN A SAMPLE MATERIAL USING ORBITAL ANGULAR MOMENTUM, now U.S. Pat. No. 9,267,877, issued Feb. 23, 2016. U.S. application Ser. Nos. 14/875,507 and 14/339,836 are incorporated by reference herein in their entirety.

TECHNICAL FIELD

The present invention relates to the detection of materials within a sample using orbital angular momentum (OAM), and more particularly, to the detection of materials within a sample based upon unique signatures of orbital angular momentum imparted to a signal passing through the sample.

BACKGROUND

Concentration measurements and detection of the presence of organic and non-organic materials is of great interest in a number of applications. In one example, detection of materials within human tissue is an increasingly important aspect of healthcare for individuals. The development of non-invasive measurement techniques for monitoring biological and metabolic agents within human tissue is an important aspect of diagnosis therapy of various human diseases and may play a key role in the proper management of diseases. The development of non-invasive measurement techniques for monitoring biological and metabolic agents within human tissue is an important aspect of diagnosis therapy of various human diseases and may play a key role in the proper management of diseases. One such material relevant to Alzheimer's is amyloid-beta. Thus, there is a need for an improved manner of amyloid-beta detection to better improve detection of early stages of Alzheimer's.

Another example of a biological agent that may be monitored for within human tissue is glucose. Glucose ($C_6H_{12}O_6$) is a monosaccharide sugar and is one of the most important carbohydrate nutrient sources. Glucose is fundamental to almost all biological processes and is required for the production of ATP adenosine triphosphate and other essential cellular components. The normal range of glucose concentration within human blood is 70-160 mg/dl depending on the time of the last meal, the extent of physical tolerance and other factors. Freely circulating glucose molecules stimulate the release of insulin from the pancreas. Insulin helps glucose molecules to penetrate the cell wall by binding two specific receptors within cell membranes which are normally impermeable to glucose.

One disease associated with issues related to glucose concentrations is diabetes. Diabetes is a disorder caused by the decreased production of insulin, or by a decreased ability to utilize insulin and transport the glucose across cell membranes. As a result, a high potentially dangerous concentration of glucose can accumulate within the blood (hyperglycemia) during the disease. Therefore, it is of great importance to maintain blood glucose concentration within a normal range in order to prevent possible severe physiological complications.

One significant role of physiological glucose monitoring is the diagnosis and management of several metabolic diseases, such as diabetes mellitus (or simply diabetes). There are a number of invasive and non-invasive techniques presently used for glucose monitoring. The problem with existing non-invasive glucose monitoring techniques is that a clinically acceptable process has not yet been determined. Standard techniques from the analysis of blood currently involve an individual puncturing a finger and subsequent analysis of collected blood samples from the finger. In recent decades, non-invasive blood glucose monitoring has become an increasingly important topic of investigation in the realm of biomedical engineering. In particular, the introduction of optical approaches has caused some advances within the field. Advances in optics have led to a focused interest in optical imaging technologies and the development of non-invasive imaging systems. The application of optical methods to monitoring in cancer diagnostics and treatment is also a growing field due to the simplicity and low risk of optical detection methods. In addition to the medical field, the detection of various types of materials in a variety of other environments would be readily apparent.

Many optical techniques for sensing different tissue metabolites and glucose in living tissue have been in development over the last 50 years. These methods have been based upon fluorescent, near infrared and mid-infrared spectroscopy, Raman spectroscopy, photoacoustics, optical coherence tomography and other techniques. However, none of these techniques that have been tried have proved completely satisfactory.

Another organic component lending itself to optical material concentration sensing involves is human skin. The defense mechanisms of human skin are based on the action of antioxidant substances such as carotenoids, vitamins and enzymes. Beta carotene and lycopene represent more than 70% of the carotenoids in the human organism. The topical or systematic application of beta carotene and lycopene is a general strategy for improving the defense system of the human body. The evaluation and optimization of this treatment requires the measurement of the b-carotene and lycopene concentrations in human tissue, especially in the human skin as the barrier to the environment.

Thus, an improved non-invasive technique enabling the detection of concentrations and presence of various materials within a human body or other types of samples would have a number of applications within the medical field.

SUMMARY

The present invention, as disclosed and described herein, in one embodiment thereof, an apparatus for identifying a material within a sample comprising signal generation circuitry generates a first signal including a first orbital angular momentum (OAM) signature and applies the first signal to the sample. A detector receives the first signal after the first signal passes through the sample and identifies the material within the sample based on a detected second orbital angular momentum caused by an interaction of the first signal with chiral molecules within the sample.

BRIEF DESCRIPTION OF THE DRAWINGS

For a more complete understanding, reference is now made to the following description taken in conjunction with the accompanying drawings in which:

FIG. 1 illustrates the manner for using an Orbital Angular Momentum signature to detect the presence of a material within a sample;

FIG. 2 illustrates the manner in which an OAM generator generates an OAM twisted beam;

FIGS. 15A-15D illustrate various holograms for use in applying an orbital angular momentum to a plane wave signal;

DETAILED DESCRIPTION

Figure 3:
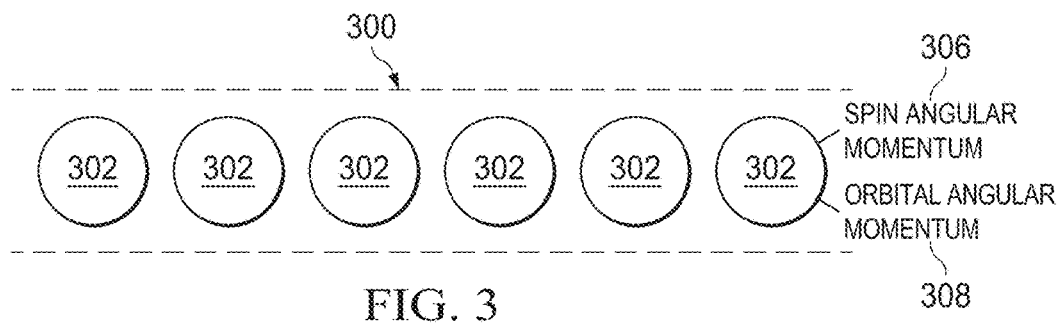
FIG. 3 illustrates a light beam having orbital angular momentum imparted thereto.

Referring now to the drawings, wherein like reference numbers are used herein to designate like elements throughout, the various views and embodiments of a system and method for detecting materials using orbital angular momentum signatures are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to the drawings, and more particularly to FIG. 1, there is illustrated the manner for detecting the presence of a particular material within a sample based upon the unique orbital angular momentum signature imparted to a signal passing through the sample. An optical signal 102 having a series of plane waves therein is applied to a device for applying an orbital angular momentum (OAM) signal to the optical signal 102 such as a spatial light modulator (SLM) 104. While the present embodiment envisions the use of an optical signal 102, other types of signals having orbital angular momentum or other orthogonal signals therein may be utilized in alternative embodiments. The SLM 104 generates an output signal 106 having a known OAM twist applied to the signal. The OAM twist has known characteristics that act as a baseline prior to the application of the output signal 106 to a sample 108. The sample 108 may comprise a material contained within a holding container, such as a cuvette, or may be a material in its natural state, such as the eye or body of a patient or its naturally occurring location in nature. The sample 108 only indicates that a particular material or item of interest is being detected by the describe system. While passing through the sample 108, the output signal 106 has a unique OAM signature applied thereto that is provided as an OAM distinct signature signal 110. OAM beams have been observed to exhibit unique topological evolution upon interacting with chiral solutions. While it has been seen that chiral molecules create unique OAM signatures when an OAM beam is passed through a sample of the chiral material, the generation of unique OAM signatures from signals passing through non-chiral molecules/material may also be provided. Given these unique topological features one can detect the existence of a molecule in a given solution with specific signatures in both the amplitude and phase measurements. This distinct signature signal 110 may then be examined using for example a camera 112 in order to detect the unique signal characteristics applied thereto and determine the material within the sample based upon this unique signature. Detection of different molecules can be applied to different industries including, but not limited to, food, chemicals, pharma and medical testings where non-invasive solutions are critical. The determination of the particular material indicated by the unique signature may be determined in one embodiment by comparison of the signature to a unique database of signatures that include known signatures that are associated with a particular material or concentration. The manner of creating such a database would be known to one skilled in the art.

Referring now to FIG. 2 illustrates the manner in which an OAM generator 220 may generate an OAM twisted beam 222. The OAM generator 210 may use any number of devices to generate the twisted beam 222 including holograms with an amplitude mask, holograms with a phase mask, Spatial Light Modulators (SLMs) or Digital Light Processors (DLPs). The OAM generator 220 receives a light beam 221 (for example from a laser) that includes a series of plane waves. The OAM generator 220 applies an orbital angular momentum to the beam 222. The beam 222 includes a single OAM mode as illustrated by the intensity diagram 223. The OAM twisted beam 222 is passed through a sample 224 including material that is being detected. As mentioned previously the sample 224 may be in a container or its naturally occurring location. The presence of the material within the sample 224 will create new OAM mode levels within the intensity diagram 225. Once the beam 222 passes through the sample 224, the output beam 226 will have three distinct signatures associated therewith based on a detection of a particular material at a particular concentration. These signatures include a change in eccentricity 228 of the intensity pattern, a shift or translation 230 in the center of gravity of the intensity pattern and a rotation 232 in three general directions ($\alpha, \beta, \gamma$) of the ellipsoidal intensity pattern output. Each of these distinct signature indications may occur in any configuration and each distinct signature will provide a unique indication of the presence of particular materials and the concentrations of these detected materials. These three distinct signatures will appear when a molecule under measurement is detected and the manner of change of these signatures represents concentration levels. The detection of the helicity spectrums from the beam passing through the sample 224 involves detecting the helical wave scatters (forward and backward) from the sample material.

The use of the OAM of light for the metrology of glucose, amyloid beta and other chiral materials has been demonstrated using the above-described configurations. OAM beams are observed to exhibit unique topological evolution upon interacting with chiral solutions within 3 cm optical path links. It should be realized that unique topological evolution may also be provided from non-chiral materials. Chiral solution, such as Amyloid-beta, glucose and others, have been observed to cause orbital angular momentum (OAM) beams to exhibit unique topological evolution when interacting therewith. OAM is not typically carried by naturally scattered photons which make use of the twisted beams more accurate when identifying the helicities of chiral molecules because OAM does not have ambient light scattering (noise) in its detection. Thus, the unique OAM signatures imparted by a material is not interfered with by ambient light scattering (noise) that does not carry OAM in naturally scattered photons making detection much more accurate. Given these unique topological features one can detect the amyloid-beta presence and concentration within a given sample based upon a specific signature in both amplitude and phase measurements. Molecular chirality signifies a structural handedness associated with variance under spatial inversion or a combination of inversion and rotation, equivalent to the usual criteria of a lack of any proper axes of rotation. Something is chiral when something cannot be made identical to its reflection. Chiral molecules that are not superimposable on their mirror image are known as Enantiomers. Traditionally, chiral optics engages circularly polarized light, even in the case of optical rotation, interpretation of the phenomenon commonly requires the plane polarized state to be understood as a superposition of circular polarizations with opposite handedness. For circularly polarized light, the left and right forms designate the sign of intrinsic spin angular momentum, $\pm h$ and also the helicity of the locus described by the associated electromagnetic field vectors. For this reason its interactions with matter are enantiomerically specific.

The continuous symmetry measure (CSM) is used to evaluate the degree of symmetry of a molecule, or the chirality. This value ranges from 0 to 100. The higher the symmetry value of a molecule the more symmetry distorted the molecule and the more chiral the molecule. The measurement is based on the minimal distance between the chiral molecule and the nearest achiral molecule.

The continuous symmetry measure may be achieved according to the equation:

$$S(G) = 100 \times \min \frac{1}{Nd^2} \sum_{k=1}^{N} |Q_k - \hat{Q}_k|^2$$

$Q_k$: The original structure
$\hat{Q}_k$: The symmetry-operated structure
N: Number of vertices
d: Size normalization factor
*The scale is 0-1 (0-100):
The larger S(G) is, the higher is the deviation from G-symmetry SG as a continuous chirality measure may be determined according to:

$$S(G) = 100 \times \min \frac{1}{Nd^2} \sum_{k=1}^{N} |Q_k - \hat{Q}_k|^2$$

G: The achiral symmetry point group which minimizes S(G)
Achiral molecule: S(G)=0

An achiral molecule has a value of S(G)=0. The more chiral a molecule is the higher the value of S(G).

The considerable interest in orbital angular momentum has been enhanced through realization of the possibility to engineer optical vortices. Here, helicity is present in the wave-front surface of the electromagnetic fields and the associated angular momentum is termed "orbital". The radiation itself is commonly referred to as a 'twisted' or 'helical' beam. Mostly, optical vortices have been studied only in their interactions with achiral matter—the only apparent exception is some recent work on liquid crystals. It is timely and of interest to assess what new features, if any, can be expected if such beams are used to interrogate any system whose optical response is associated with enantiomerically specific molecules.

First the criteria for manifestations of chirality in optical interactions are constructed in generalized form. For simplicity, materials with a unique enantiomeric specificity are assumed—signifying a chirality that is intrinsic and common to all molecular components (or chromophores) involved in the optical response. Results for systems of this kind will also apply to single molecule studies. Longer range translation/rotation order can also produce chirality, as for example in twisted nematic crystals, but such mesoscopic chirality cannot directly engender enantiomerically specific interactions. The only exception is where optical waves probe two or more electronically distinct, dissymmetrically oriented but intrinsically achiral molecules or chromophores.

Chiroptical interactions can be distinguished by their electromagnetic origins: for molecular systems in their usual singlet electronic ground state, they involve the spatial variation of the electric and magnetic fields associated with the input of optical radiation. This variation over space can be understood to engage chirality either through its coupling with di-symmetrically placed, neighboring chromophore groups (Kirkwood's two-group model, of limited application) or more generally through the coupling of its associated electric and magnetic fields with individual groups. As chirality signifies a local breaking of parity it permits an interference of electric and magnetic interactions. Even in the two group case, the paired electric interactions of the system correspond to electric and magnetic interactions of the single entity which the two groups comprise. Thus, for convenience, the term 'chiral center' is used in the following to denote either chromophore or molecule.

With the advent of the laser, the Gaussian beam solution to the wave equation came into common engineering parlance, and its extension two higher order laser modes, Hermite Gaussian for Cartesian symmetry; Laguerre Gaussian for cylindrical symmetry, etc., entered laboratory optics operations. Higher order Laguerre Gaussian beam modes exhibit spiral, or helical phase fronts. Thus, the propagation vector, or the eikonal of the beam, and hence the beams momentum, includes in addition to a spin angular momentum, an orbital angular momentum, i.e. a wobble around the sea axis. This phenomenon is often referred to as vorticity. The expression for a Laguerre Gaussian beam is given in cylindrical coordinates:

$$u(r, \theta, z) = \sqrt{\frac{2pl}{1 + \delta_{0,m}\pi(m+p)!}} \frac{1}{w(z)}$$

$$\exp[j(2p + m + 1)(\psi(z) - \psi_0)] \left(\frac{\sqrt{2}r}{w(z)}\right) L_p^m \left(\frac{2r^2}{w(z)^2}\right) \exp\left[-jk\frac{r^2}{2q(z)} + im\theta\right]$$

Here, w(x) is the beam spot size, q(c) is the complex beam parameter comprising the evolution of the spherical wave front and the spot size. Integers p and m are the radial and azimuthal modes, respectively. The exp(imθ) term describes the spiral phase fronts.

Referring now also to FIG. 3, there is illustrated one embodiment of a beam for use with the system. A light beam 300 consists of a stream of photons 302 within the light beam 300. Each photon has an energy ±ℏω and a linear momentum of ±ℏk which is directed along the light beam axis 304 perpendicular to the wavefront. Independent of the frequency, each photon 302 within the light beam has a spin angular momentum 306 of ±ℏ aligned parallel or antiparallel to the direction of light beam propagation. Alignment of all of the photons 302 spins gives rise to a circularly polarized light beam. In addition to the circular polarization, the light beams also may carry an orbital angular momentum 308 which does not depend on the circular polarization and thus is not related to photon spin.

Figure 4:
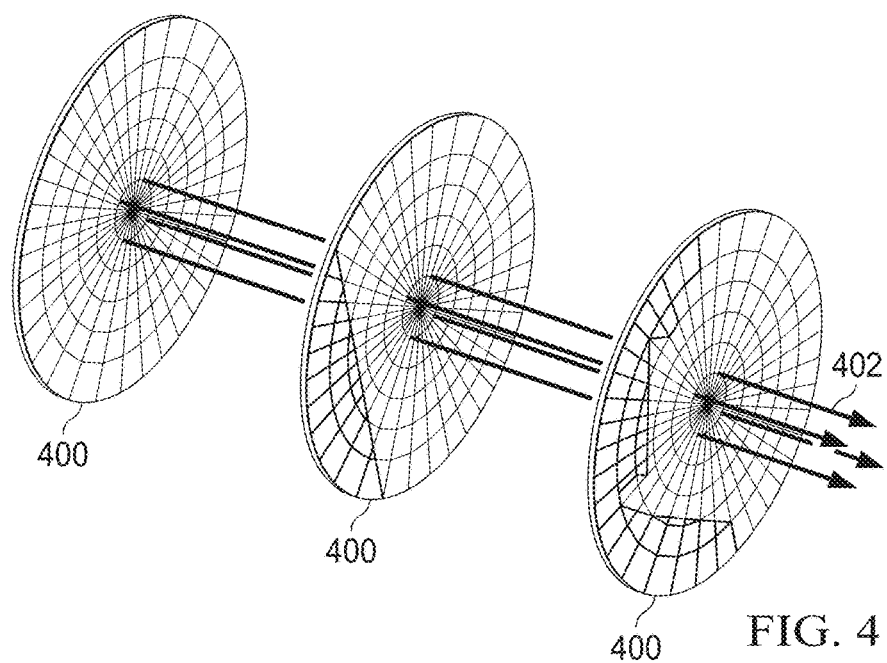
FIG. 4 illustrates a series of parallel wavefronts.

Lasers are widely used in optical experiments as the source of well-behaved light beams of a defined frequency. A laser may be used for providing the light beam 300. The energy flux in any light beam 300 is given by the Poynting vector which may be calculated from the vector product of the electric and magnetic fields within the light beam. In a vacuum or any isotropic material, the Poynting vector is parallel to the wave vector and perpendicular to the wavefront of the light beam. In a normal laser light, the wavefronts 400 are parallel as illustrated in FIG. 4. The wave vector and linear momentum of the photons are directed along the axis in a z direction 402. The field distributions of such light beams are paraxial solutions to Maxwell's wave equation but although these simple beams are the most common, other possibilities exist.

Figure 5:
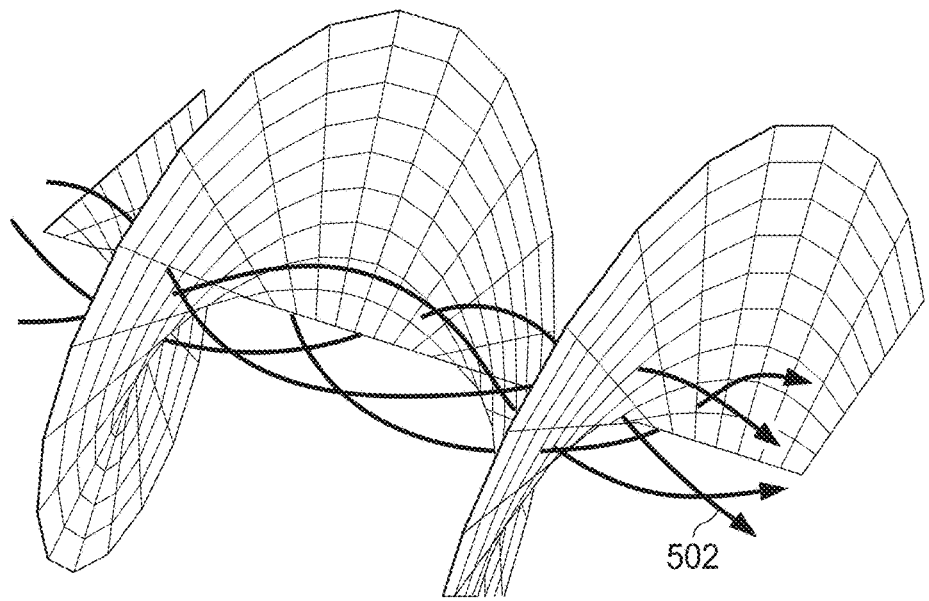
FIG. 5 illustrates a wavefront having a Poynting vector spiraling around a direction of propagation of the wavefront.

For example, beams that have l intertwined helical fronts are also solutions of the wave equation. The structure of these complicated beams is difficult to visualize, but their form is familiar from the l=3 fusilli pasta. Most importantly, the wavefront has a Poynting vector and a wave vector that spirals around the light beam axis direction of propagation as illustrated in FIG. 5 at 502.

A Poynting vector has an azimuthal component on the wave front and a non-zero resultant when integrated over the beam cross-section. The spin angular momentum of circularly polarized light may be interpreted in a similar way. A beam with a circularly polarized planer wave front, even though it has no orbital angular momentum, has an azimuthal component of the Poynting vector proportional to the radial intensity gradient. This integrates over the cross-section of the light beam to a finite value. When the beam is linearly polarized, there is no azimuthal component to the Poynting vector and thus no spin angular momentum.

Thus, the momentum of each photon 302 within the light beam 300 has an azimuthal component. A detailed calculation of the momentum involves all of the electric fields and magnetic fields within the light beam, particularly those electric and magnetic fields in the direction of propagation of the beam. For points within the beam, the ratio between the azimuthal components and the z components of the momentum is found to be l/kr. (where l=the helicity or orbital angular momentum; k=wave number $2\pi/\lambda$; r=the radius vector.) The linear momentum of each photon 302 within the light beam 300 is given by $\hbar k$, so if we take the cross product of the azimuthal component with a radius vector, r, we obtain an orbital momentum for a photon 602 of $l\hbar$. Note also that the azimuthal component of the wave vectors is l/r and independent of the wavelength.

Figure 6:
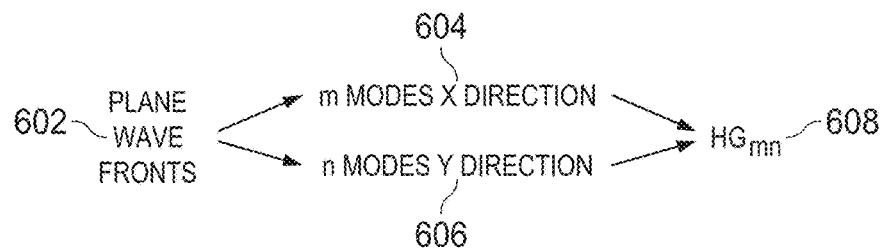
FIG. 6 illustrates a plane wavefront.
Figure 7:
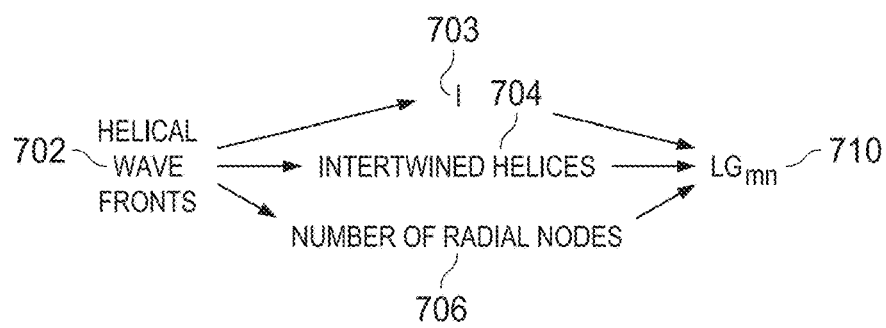
FIG. 7 illustrates a helical wavefront.

Referring now to FIGS. 6 and 7, there are illustrated plane wavefronts and helical wavefronts. Ordinarily, laser beams with plane wavefronts 602 are characterized in terms of Hermite-Gaussian modes. These modes have a rectangular symmetry and are described by two mode indices m 604 and n 606. There are m nodes in the x direction and n nodes in the y direction. Together, the combined modes in the x and y direction are labeled $HG_{mn}$ 608. In contrast, as shown in FIG. 7, beams with helical wavefronts 702 are best characterized in terms of Laguerre-Gaussian modes which are described by indices l 703, the number of intertwined helices 704, and p, the number of radial nodes 706. The Laguerre-Gaussian modes are labeled $LG_{mn}$ 710. For l≠0, the phase singularity on a light beam 300 results in 0 on axis intensity. When a light beam 300 with a helical wavefront is also circularly polarized, the angular momentum has orbital and spin components, and the total angular momentum of the light beam is $(l\pm\hbar)$ per photon.

Using the orbital angular momentum state of the transmitted energy signals, physical information can be embedded within the electromagnetic radiation transmitted by the signals. The Maxwell-Heaviside equations can be represented as:

$$\nabla \cdot E = \frac{\rho}{\varepsilon_0}$$

$$\nabla \times E = -\frac{\partial B}{\partial t}$$

$$\nabla \cdot B = 0$$

$$\nabla \times B = \varepsilon_0 \mu_0 \frac{\partial E}{\partial t} + \mu_0 j(t, x) \text{the}$$

where $\nabla$ is the del operator, E is the electric field intensity and B is the magnetic flux density. Using these equations, we can derive 23 symmetries/conserve quantities from Maxwell's original equations. However, there are only ten well-known conserve quantities and only a few of these are commercially used. Historically if Maxwell's equations where kept in their original quaternion forms, it would have been easier to see the symmetries/conserved quantities, but when they were modified to their present vectorial form by Heaviside, it became more difficult to see such inherent symmetries in Maxwell's equations.

The conserved quantities and the electromagnetic field can be represented according to the conservation of system energy and the conservation of system linear momentum. Time symmetry, i.e. the conservation of system energy can be represented using Poynting's theorem according to the equations:

$$H = \sum_i m_i \gamma_i c^2 + \frac{\varepsilon_0}{2} \int d^3x (|E|^2 + c^2|B|^2)$$

$$\frac{dU^{mech}}{dt} + \frac{dU^{em}}{d} + \oint_{S'} d^2x' \hat{n}' \cdot S = 0$$

The space symmetry, i.e., the conservation of system linear momentum representing the electromagnetic Doppler shift can be represented by the equations:

$$P = \sum_i m_i \gamma_i v_i + \varepsilon_0 \int d^3x (E \times B)$$

$$\frac{dp^{mech}}{dt} + \frac{dp^{em}}{dt} + \oint_{S'} d^2x' \hat{n}'. \ T = 0$$

The conservation of system center of energy is represented by the equation:

$$R = \frac{1}{H} \sum_i (x_i - x_0) m_i \gamma_i c^2 + \frac{\varepsilon_0}{2H} \int d^3x (x - x_0)(|E|^2 + c^2|B^2|)$$

Similarly, the conservation of system angular momentum, which gives rise to the azimuthal Doppler shift is represented by the equation:

$$\frac{dJ^{mech}}{dt} + \frac{dJ^{em}}{dt} + \oint_{S'} d^2x' \hat{n}'. \ M = 0$$

For radiation beams in free space, the EM field angular momentum $J^{em}$ can be separated into two parts:

$$J^{em} = \varepsilon_0 \int_{V'} d^3x' (E \times A) + \varepsilon_0 \int_{V'} d^3x' E_i [(x' - x_0) \times \nabla] A_i$$

For each singular Fourier mode in real valued representation:

$$J^{em} = -i\frac{\varepsilon_0}{2\omega} \int_{V'} d^3x' (E^* \times E) - i\frac{\varepsilon_0}{2\omega} \int_{V'} d^3x' E_i [(x' - x_0) \times \nabla] E_i$$

The first part is the EM spin angular momentum $S^{em}$, its classical manifestation is wave polarization. And the second part is the EM orbital angular momentum $L^{em}$ its classical manifestation is wave helicity. In general, both EM linear momentum $P^{em}$, and EM angular momentum $J^{em} = L^{em} + S^{em}$ are radiated all the way to the far field.

By using Poynting theorem, the optical vorticity of the signals may be determined according to the optical velocity equation:

$$\frac{\partial U}{\partial t} + \nabla \cdot S = 0$$

where S is the Poynting vector $$S = \tfrac{1}{4}(E \times H^* + E^* \times H)$$

and U is the energy density $$U = \tfrac{1}{4}(\varepsilon|E|^2 + \mu_0|H|^2)$$

with E and H comprising the electric field and the magnetic field, respectively, and $\varepsilon$ and $\mu_0$ being the permittivity and the permeability of the medium, respectively. The optical vorticity V may then be determined by the curl of the optical velocity according to the equation:

$$V = \nabla \times v_{opt} = \nabla \times \left( \frac{E \times H^* + E^* \times H}{\varepsilon|E|^2 + \mu_0|H|^2} \right)$$

Figure 8:
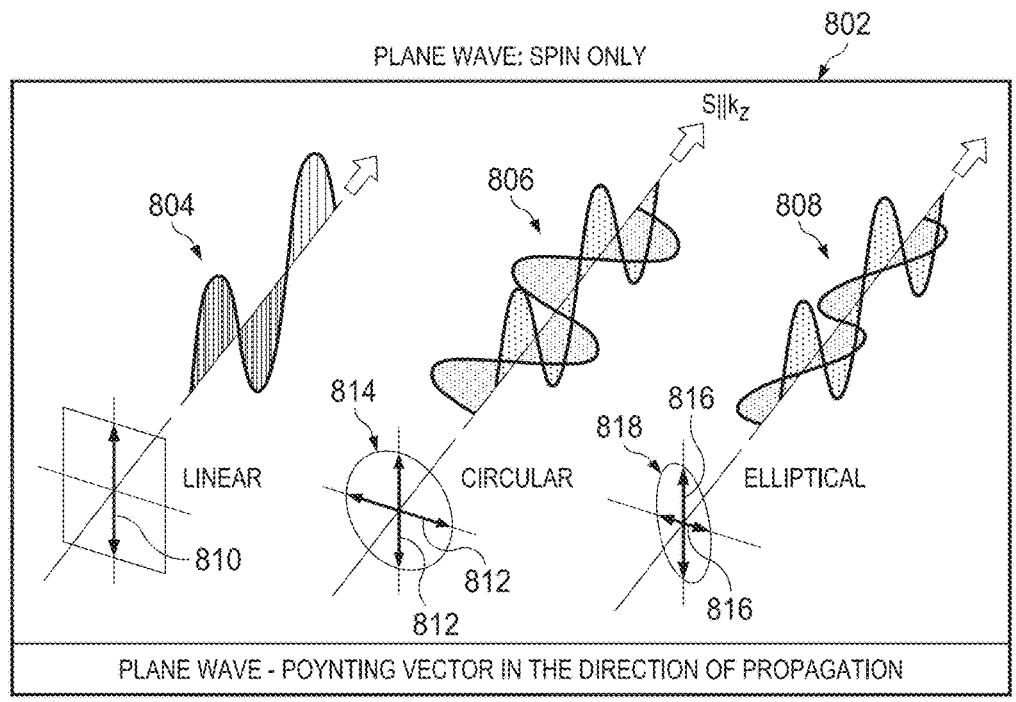
FIG. 8 illustrates a plane wave having only variations in the spin vector.
Figure 9:
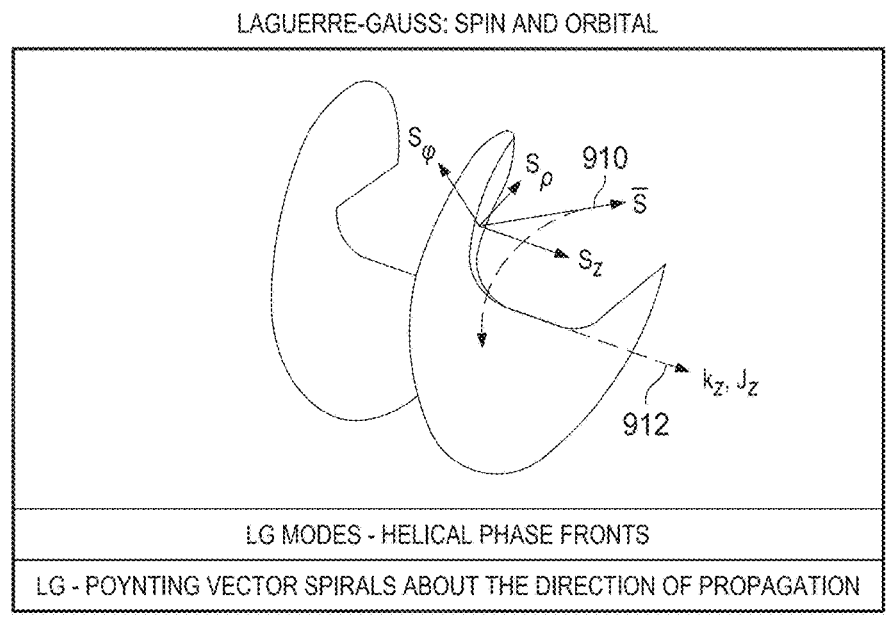
FIG. 9 illustrates the application of a unique orbital angular momentum to a wave.

Referring now to FIGS. 8 and 9, there are illustrated the manner in which a signal and an associated Poynting vector of the signal vary in a plane wave situation (FIG. 8) where only the spin vector is altered, and in a situation wherein the spin and orbital vectors are altered in a manner to cause the Poynting vector to spiral about the direction of propagation (FIG. 9).

In the plane wave situation, illustrated in FIG. 8, when only the spin vector of the plane wave is altered, the transmitted signal may take on one of three configurations. When the spin vectors are in the same direction, a linear signal is provided as illustrated generally at 804. It should be noted that while 804 illustrates the spin vectors being altered only in the x direction to provide a linear signal, the spin vectors can also be altered in the y direction to provide a linear signal that appears similar to that illustrated at 804 but in a perpendicular orientation to the signal illustrated at 804. In linear polarization such as that illustrated at 804, the vectors for the signal are in the same direction and have a same magnitude.

Within a circular polarization as illustrated at 806, the signal vectors 812 are 90 degrees to each other but have the same magnitude. This causes the signal to propagate as illustrated at 806 and provide the circular polarization 814 illustrated in FIG. 8. Within an elliptical polarization 808, the signal vectors 816 are also 90 degrees to each other but have differing magnitudes. This provides the elliptical polarizations 818 illustrated for the signal propagation 408. For the plane waves illustrated in FIG. 8, the Poynting vector is maintained in a constant direction for the various signal configurations illustrated therein.

The situation in FIG. 9 illustrates when a unique orbital angular momentum is applied to a signal. When this occurs, Poynting vector S 910 will spiral around the general direction of propagation 912 of the signal. The Poynting vector 910 has three axial components $S_\varphi$, $S_p$ and $S_z$ which vary causing the vector to spiral about the direction of propagation 912 of the signal. The changing values of the various vectors comprising the Poynting vector 910 may cause the spiral of the Poynting vector to be varied in order to enable signals to be transmitted on a same wavelength or frequency as will be more fully described herein. Additionally, the values of the orbital angular momentum indicated by the Poynting vector 910 may be measured to determine the presence of particular materials and the concentrations associated with particular materials being processed by a scanning mechanism.

Figure 10A:
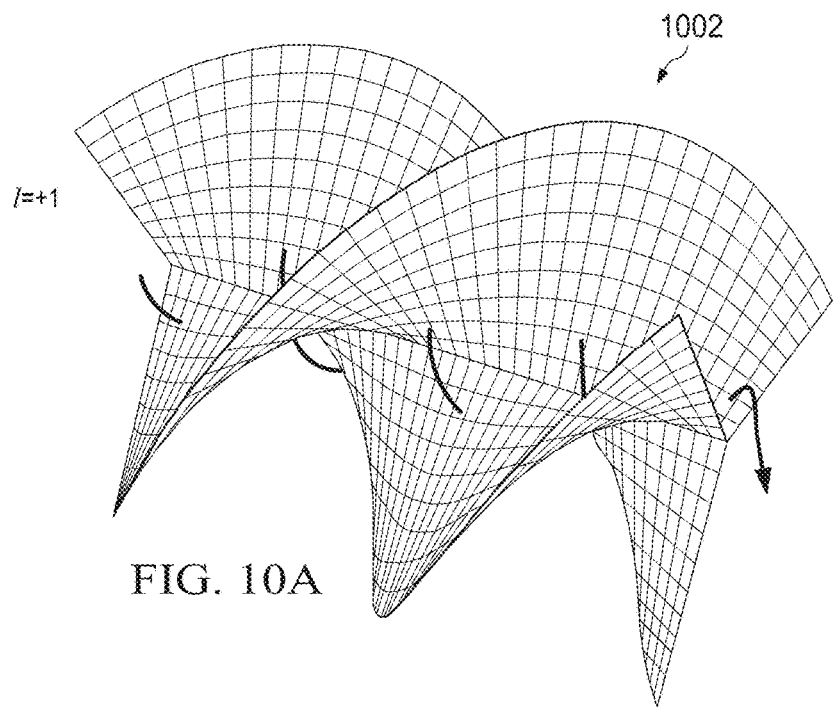
FIGS. 10A-10C illustrate the differences between signals having different orbital angular momentum applied thereto.
Figure 10B:
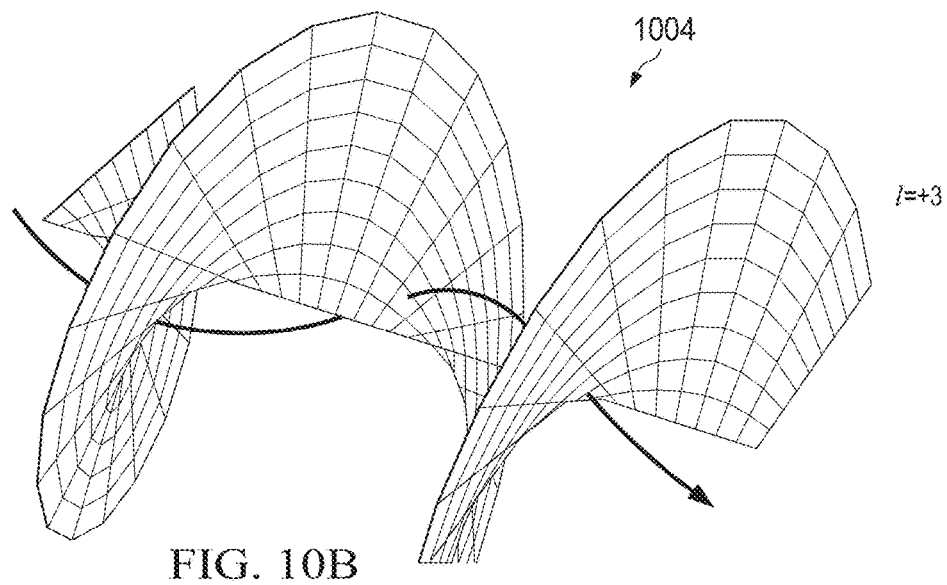
Figure 10C:
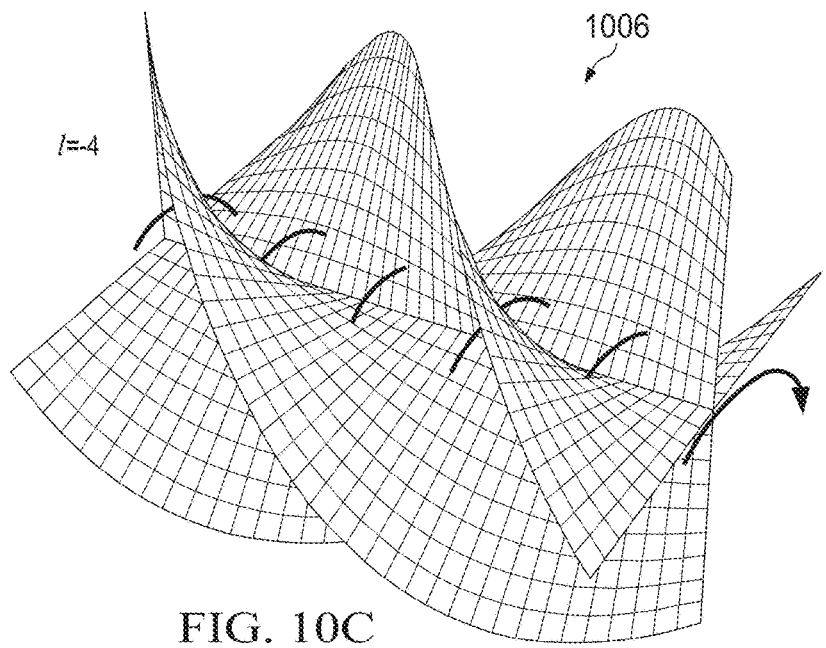

FIGS. 10A-10C illustrate the differences in signals having a different helicity (i.e., orbital angular momentum applied thereto). The differing helicities would be indicative of differing materials and concentration of materials within a sample that a beam was being passed through. By determining the particular orbital angular momentum signature associated with a signal, the particular material and concentration amounts of the material could be determined. Each of the spiraling Poynting vectors associated with a signal 1002, 1004 and 1006 provides a different-shaped signal. Signal 1002 has an orbital angular momentum of +1, signal 1004 has an orbital angular momentum of +3 and signal 1006 has an orbital angular momentum of −4. Each signal has a distinct orbital angular momentum and associated Poynting vector enabling the signal to be indicative of a particular material and concentration of material that is associated with the detected orbital angular momentum. This allows determinations of materials and concentrations of various types of materials to be determined from a signal since the orbital angular momentums are separately detectable and provide a unique indication of the particular material and the concentration of the particular material that has affected the orbital angular momentum of the signal transmitted through the sample material.

Figure 11:
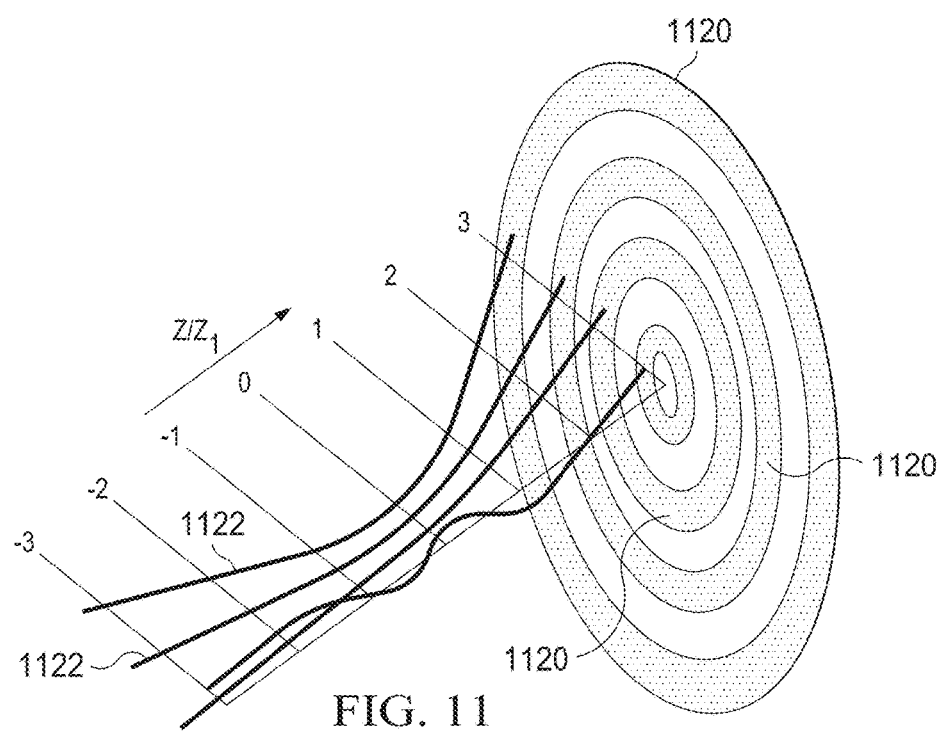
FIG. 11 illustrates the propagation of Poynting vectors for various eigenmodes.

FIG. 11 illustrates the propagation of Poynting vectors for various Eigen modes. Each of the rings 1120 represents a different Eigen mode or twist representing a different orbital angular momentum. Each of the different orbital angular momentums is associated with particular material and a particular concentration of the particular material. Detection of orbital angular momentums provides an indication of the a presence of an associated material and a concentration of the material that is being detected by the apparatus. Each of the rings 1120 represents a different material and/or concentration of a selected material that is being monitored. Each of the Eigen modes has a Poynting vector 1122 for generating the rings indicating different materials and material concentrations.

Figure 12:
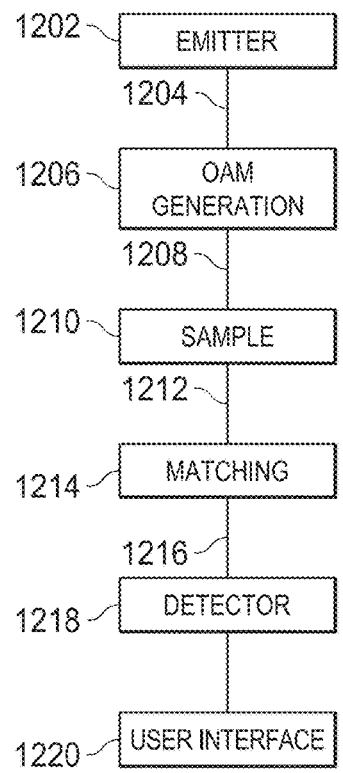
FIG. 12 illustrates a block diagram of an apparatus for providing concentration measurements and presence detection of various materials using orbital angular momentum.

Referring now to FIG. 12, there is illustrated a block diagram of the apparatus for providing detection of the presence of a material and concentration measurements of various materials responsive to the orbital angular momentum detected by the apparatus in accordance with the principles described herein above. An emitter 1202 transmits wave energy 1204 that comprises a series of plane waves. The emitter 1202 may provide a series of plane waves such as those describes previously with respect to FIG. 7. The orbital angular momentum generation circuitry 1206 generates a series of waves having an orbital angular momentum applied to the waves 1208 in a known manner. The orbital angular momentum generation circuitry 1206 may utilize holograms or some other type of orbital angular momentum generation process as will be more fully described herein below. The OAM generation circuitry 1206 may be generated by transmitting plane waves through a spatial light modulator (SLM), an amplitude mask or a phase mask. The orbital angular momentum twisted waves 1208 are applied to a sample material 1210 under test. The sample material 1210 contains a material, and the presence and concentration of the material is determined via a detection apparatus in accordance with the process described herein. The sample material 1210 may be located in a container or at its naturally occurring location in nature such as an individual's body.

A series of output waves 1212 from the sample material 1210 exit the sample and have a particular orbital angular momentum imparted thereto as a result of the material and the concentration of the particular material under study within the sample material 1210. The output waves 1212 are applied to a matching module 1214 that includes a mapping aperture for amplifying a particular orbital angular momentum generated by the specific material under study. The matching module 1214 will amplify the orbital angular momentums associated with the particular material and concentration of material that is detected by the apparatus. The amplified OAM waves 1216 are provided to a detector 1218. The detector 1218 detects OAM waves relating to the material and the concentration of a material within the sample and provides this information to a user interface 1220. The detector 1218 may utilize a camera to detect distinct topological features from the beam passing through the sample. The user interface 1220 interprets the information and provides relevant material type and concentration indication to an individual or a recording device.

Figure 13:
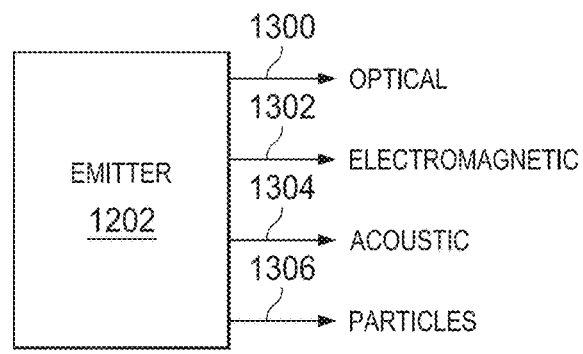
FIG. 13 illustrates an emitter of the system of FIG. 11.

Referring now to FIG. 13, there is more particularly illustrated the emitter 1202. The emitter 1202 may emit a number of types of energy waves 1204 to the OAM generation module 1206. The emitter 1202 may emit optical waves 1300, electromagnetic waves 1302, acoustic waves 1304 or any other type of particle waves 1306. The emitted waves 1204 are plane waves such as those illustrated in FIG. 4 having no orbital angular momentum applied thereto and may come from a variety of types of emission devices and have information included therein. In one embodiment, the emission device may comprise a laser. Plane waves have wavefronts that are parallel to each other having no twist or helicity applied thereto, and the orbital angular momentum of the wave is equal to 0. The Poynting vector within a plane wave is completely in line with the direction of propagation of the wave.

Figure 14:
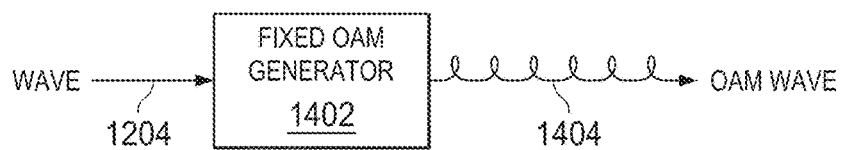
FIG. 14 illustrates a fixed orbital angular momentum generator of the system of FIG. 11.
Figure 15A:
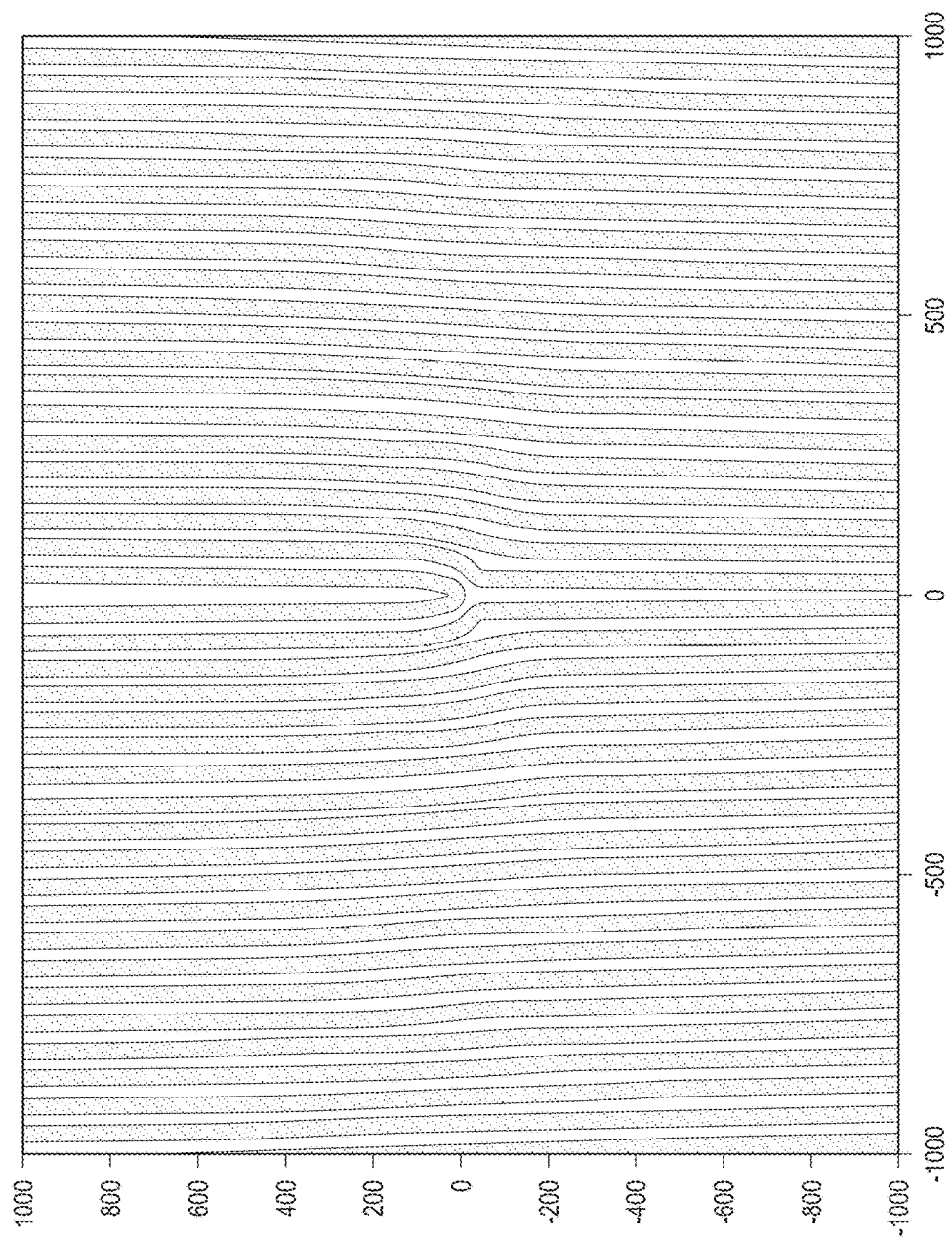
Figure 15B:
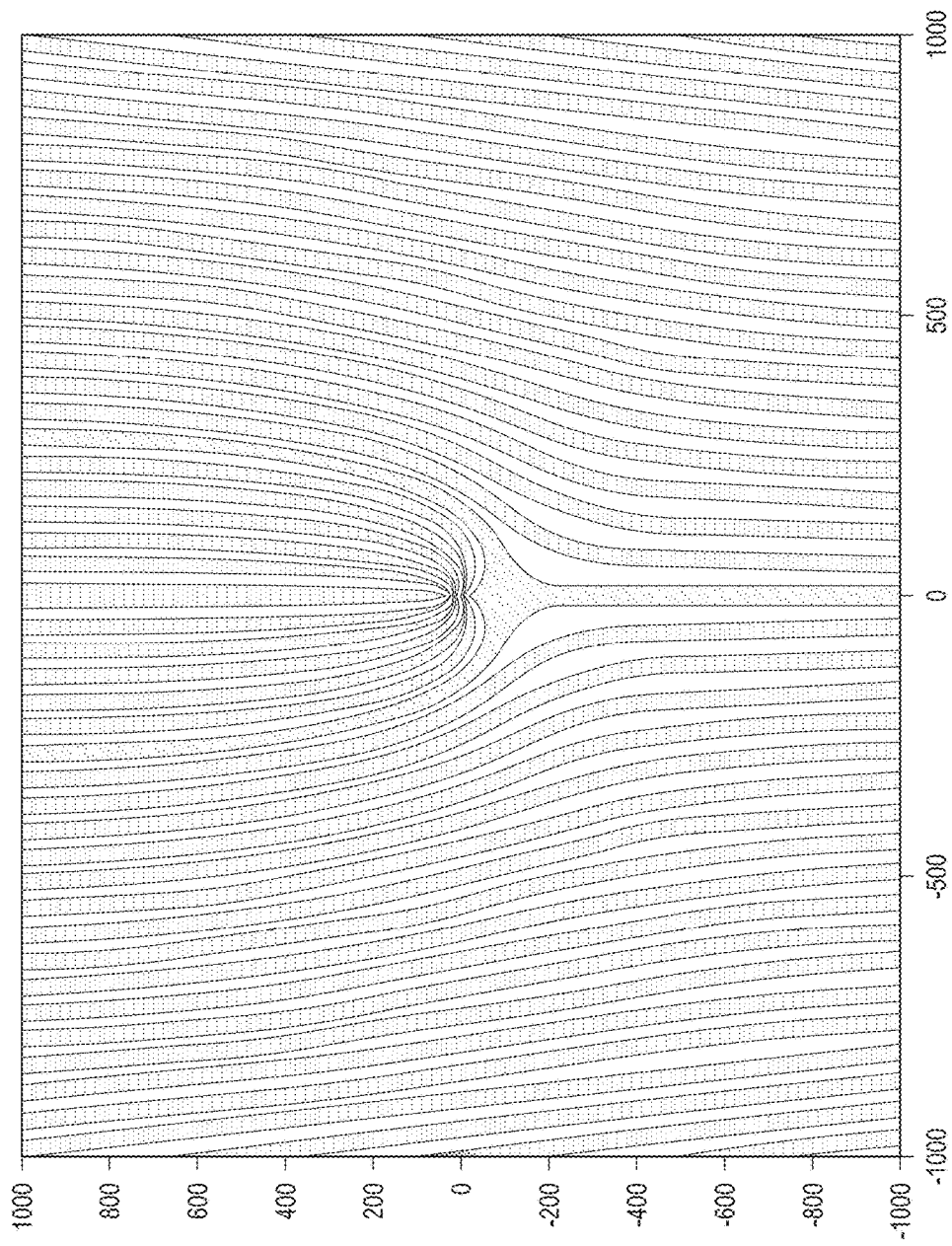
Figure 15D:
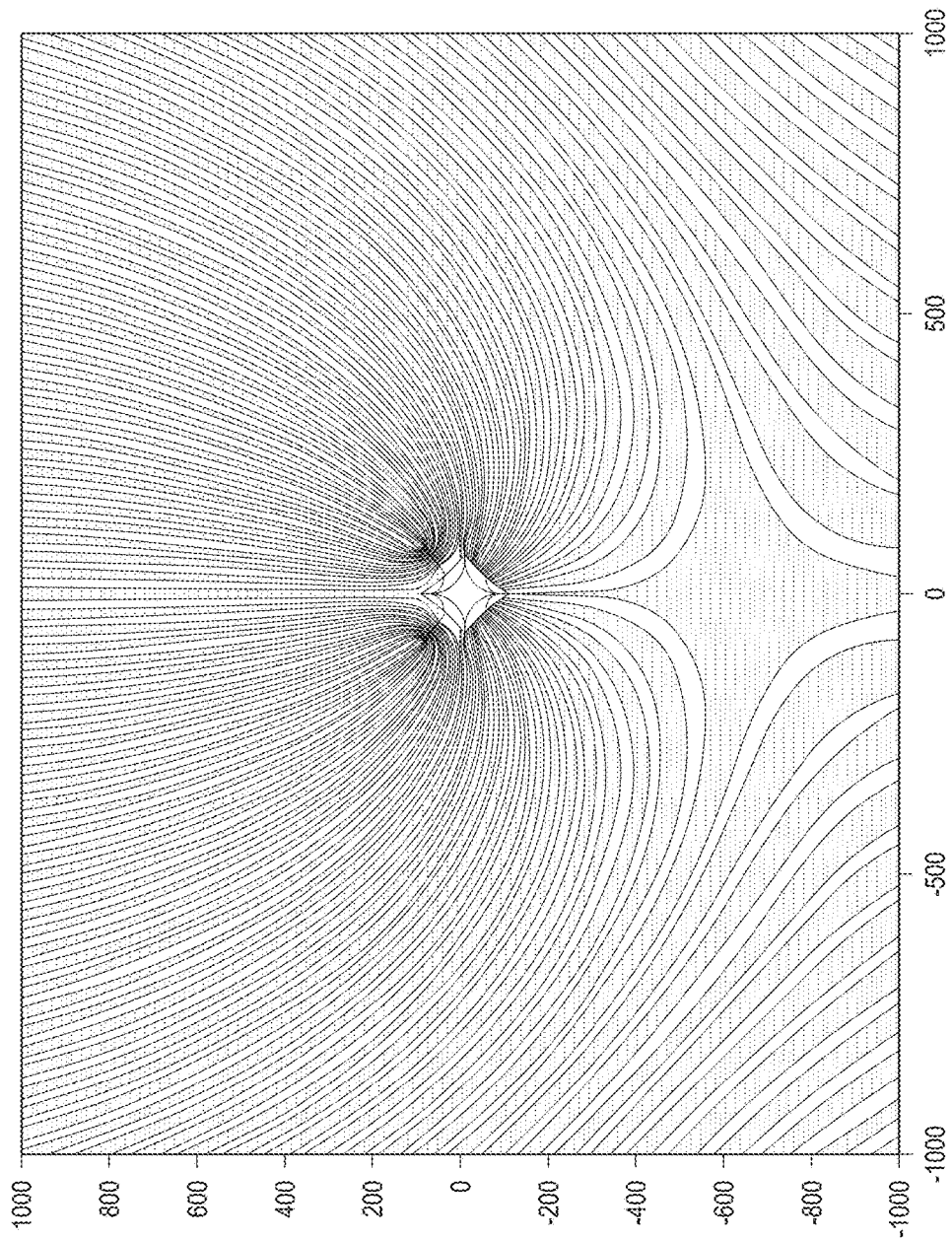

The OAM generation module 1206 processes the incoming plane wave 1204 and imparts a known orbital angular momentum onto the plane waves 1204 provided from the emitter 1202. The OAM generation module 1206 generates twisted or helical electromagnetic, optic, acoustic or other types of particle waves from the plane waves of the emitter 1202. A helical wave 1208 is not aligned with the direction of propagation of the wave but has a procession around direction of propagation as shown in FIG. 14. The OAM generation module 1206 may comprise in one embodiment a fixed orbital angular momentum generator 1402 as illustrated in FIG. 14. The fixed orbital angular momentum generator 1402 receives the plane waves 1204 from the emitter 1202 and generates an output wave 1404 having a fixed orbital angular momentum applied thereto.

The fixed orbital angular momentum generator 1402 may in one embodiment comprise a holographic image for applying the fixed orbital angular momentum to the plane wave 1204 in order to generate the OAM twisted wave 1404. Various types of holographic images may be generated in order to create the desired orbital angular momentum twist to an optical signal that is being applied to the orbital angular momentum generator 1402. Various examples of these holographic images are illustrated in FIG. 15A-15D. In one embodiment, the conversion of the plane wave signals transmitted from the emitter 1202 by the orbital angular momentum generation circuitry 1206 may be achieved using holographic images.

Figure 16:
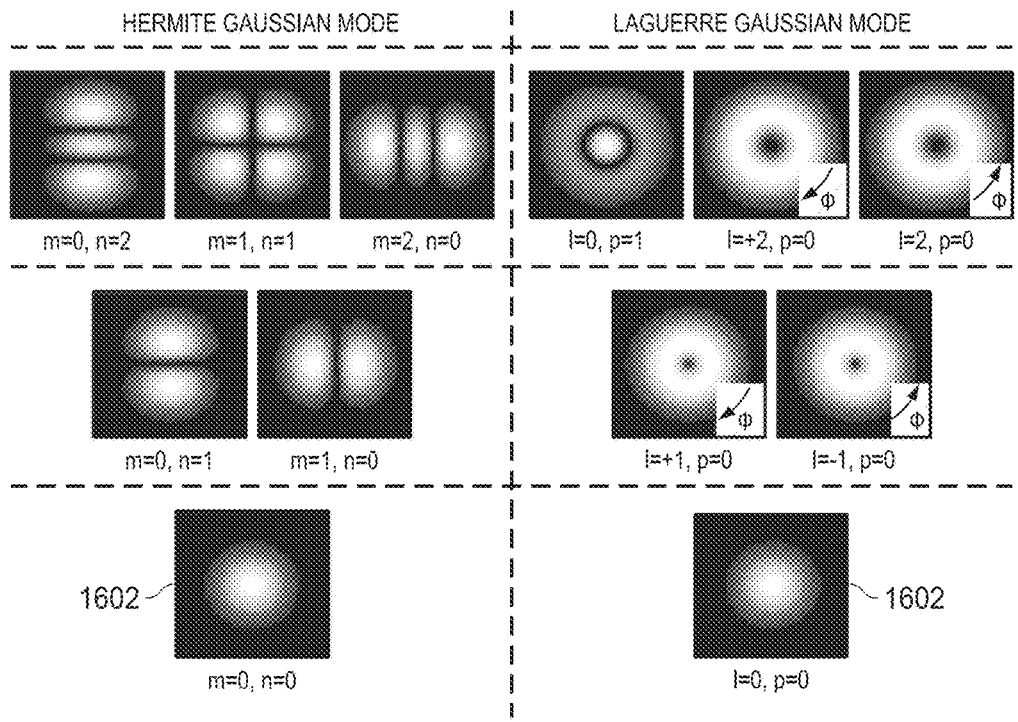
FIG. 16 illustrates the relationship between Hermite-Gaussian modes and Laguerre-Gaussian modes.

Most commercial lasers emit an $HG_{00}$ (Hermite-Gaussian) mode 1602 (FIG. 16) with a planar wave front and a transverse intensity described by a Gaussian function. Although a number of different methods have been used to successfully transform an $HG_{00}$ Hermite-Gaussian mode 1602 into a Laguerre-Gaussian mode 1604, the simplest to understand is the use of a hologram.

The cylindrical symmetric solution $u_{pl}$ (r, φ, z) which describes Laguerre-Gaussian beams, is given by the equation:

$$u_{pl}(r, \phi, z) = \frac{C}{(1+z^2/z_R^2)^{1/2}} \left[\frac{r\sqrt{2}}{w(z)}\right]^l L_p^l\left[\frac{2r^2}{w^2(z)}\right] \exp\left[\frac{-r^2}{w^2(z)}\right]$$
$$\exp\left[\frac{-ikr^2z}{2(z^2+z_R^2)}\right] \exp(-il\phi) \times \exp\left[i(2p+l+1)\tan^{-1}\frac{z}{z_R}\right]$$

Where $z_R$ is the Rayleigh range, w(z) is the radius of the beam, $L_p^l$ is the Laguerre polynomial, C is a constant, and the beam waist is at z=0.

In its simplest form, a computer generated hologram is produced from the calculated interference pattern that results when the desired beam intersects the beam of a conventional laser at a small angle. The calculated pattern is transferred to a high resolution holographic film. When the developed hologram is placed in the original laser beam, a diffraction pattern results. The first order of which has a desired amplitude and phase distribution. This is one manner for implementing the OAM generation module 1206. A number of examples of holographic images for use within a OAM generation module are illustrated with respect to FIGS. 15A-15D.

There are various levels of sophistication in hologram design. Holograms that comprise only black and white areas with no grayscale are referred to as binary holograms. Within binary holograms, the relative intensities of the two interfering beams play no role and the transmission of the hologram is set to be zero for a calculated phase difference between zero and π, or unity for a phase difference between π and 2π. A limitation of binary holograms is that very little of the incident power ends up in the first order diffracted spot, although this can be partly overcome by blazing the grating. When mode purity is of particular importance, it is also possible to create more sophisticated holograms where the contrast of the pattern is varied as a function of radius such that the diffracted beam has the required radial profile.

A plane wave shining through the holographic images 1502 will have a predetermined orbital angular momentum shift applied thereto after passing through the holographic image 1502. OAM generator 1202 is fixed in the sense that a same image is used and applied to the beam being passed through the holographic image. Since the holographic image 1502 does not change, the same orbital angular momentum is always applied to the beam being passed through the holographic image 1502. While FIGS. 15A-15D illustrate a number of embodiments of various holographic images that might be utilized within the orbital angular momentum generator 1202, it will be realized that any type of holographic image 1502 may be utilized in order to achieve the desired orbital angular momentum within an beam being shined through the image 1502.

Figure 17:
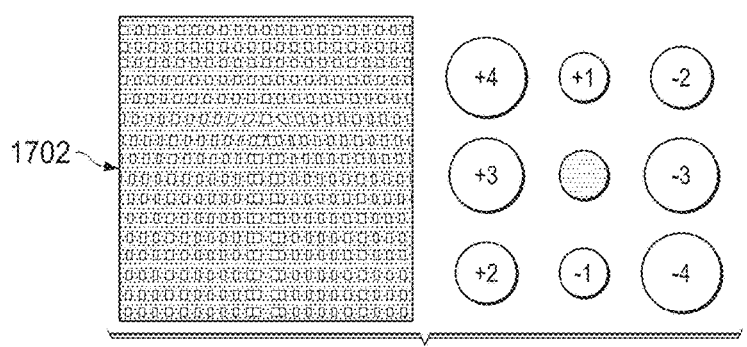
FIG. 17 illustrates super-imposed holograms for applying orbital angular momentum to a signal.

In another example of a holographic image illustrated in FIG. 17, there is illustrated a hologram that utilizes two separate holograms that are gridded together to produce a rich number of orbital angular momentum (l). The superimposed holograms of FIG. 17 have an orbital angular momentum of l=1 and l=3 which are superimposed upon each other to compose the composite vortex grid 1702. The holograms utilized may also be built in a manner that the two holograms are gridded together to produce a varied number of orbital angular momentums (l) not just on a line (l=+1, l=0, l=−1) but on a square which is able to identify the many variables more easily. Thus, in the example in FIG. 17, the orbital angular momentums along the top edge vary from +4 to +1 to −2 and on the bottom edge from +2 to −1 to −4. Similarly, along the left edge the orbital angular momentums vary from +4 to +3 to +2 and on the right edge from −2 to −3 to −4. Across the horizontal center of the hologram the orbital angular momentums provided vary from +3 to 0 to −3 and along the vertical axis vary from +1 to 0 to −1. Thus, depending upon the portion of the grid a beam may pass through, varying orbital angular momentum may be achieved.

Figure 18:
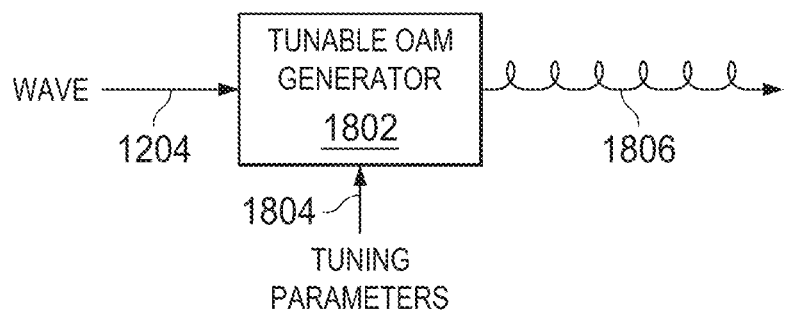
FIG. 18 illustrates a tunable orbital angular momentum generator for use in the system of FIG. 11.

Referring now to FIG. 18, in addition to a fixed orbital angular momentum generator, the orbital angular momentum generation circuitry 1206 may also comprise a tunable orbital angular momentum generator circuitry 1802. The tunable orbital angular momentum generator 1802 receives the input plane wave 1204 but additionally receives one or more tuning parameters 1804. The tuning parameters 1804 tune the tunable OAM generator 1802 to apply a selected orbital angular momentum so that the tuned OAM wave 1806 that is output from the OAM generator 1802 has a selected orbital angular momentum value applied thereto.

This may be achieved in any number of fashions. In one embodiment, illustrated in FIG. 22, the tunable orbital angular momentum generator 1802 may include multiple hologram images 2202 within the tunable OAM generator 1802. The tuning parameters 1804 enable selection of one of the holographic images 2206 in order to provide the desired OAM wave twisted output signal 1806 through a selector circuit 2204. Alternatively, the gridded holographic image such as that described in FIG. 16 may be utilized and the beam shined on a portion of the gridded image to provide the desired OAM output. The tunable OAM generator 1802 has the advantage of being controlled to apply a particular orbital angular momentum to the output orbital angular momentum wave 1806 depending upon the provided input parameter 1804. This enables the presence and concentrations of a variety of different materials to be monitored, or alternatively, for various different concentrations of the same material to be monitored.

Figure 19:
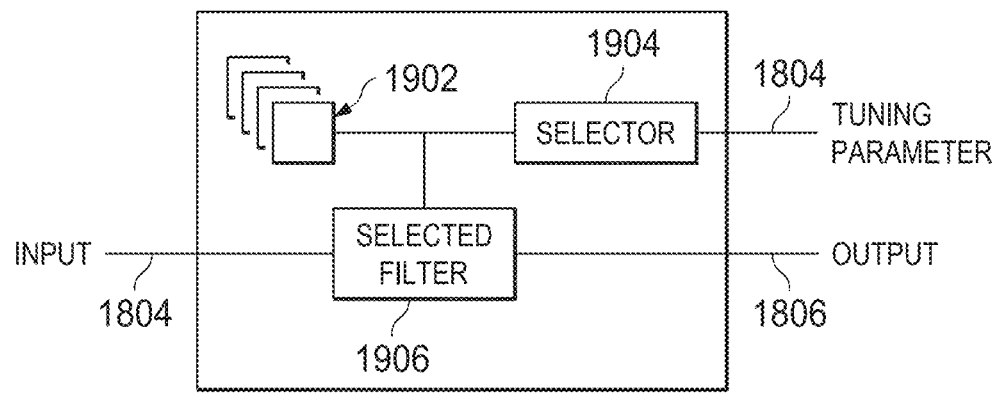
FIG. 19 illustrates a block diagram of a tunable orbital angular momentum generator including multiple hologram images therein.

Referring now to FIG. 19, there is more particularly implemented a block diagram of a tunable orbital angular momentum generator 1802. The generator 1802 includes a plurality of holographic images 1902 for providing orbital angular momentums of various types to a provided light signal. These holographic images 1902 are selected responsive to a selector circuitry 1904 that is responsive to the input tuning parameters 1804. The selected filter 1906 comprises the holographic image that has been selected responsive to the selector controller 1904 and receives the input plane waves 1204 to provide the tuned orbital angular momentum wave output 1206. In this manner, signals having a desired orbital angular momentum may be output from the OAM generation circuitry 1206.

Figure 20:
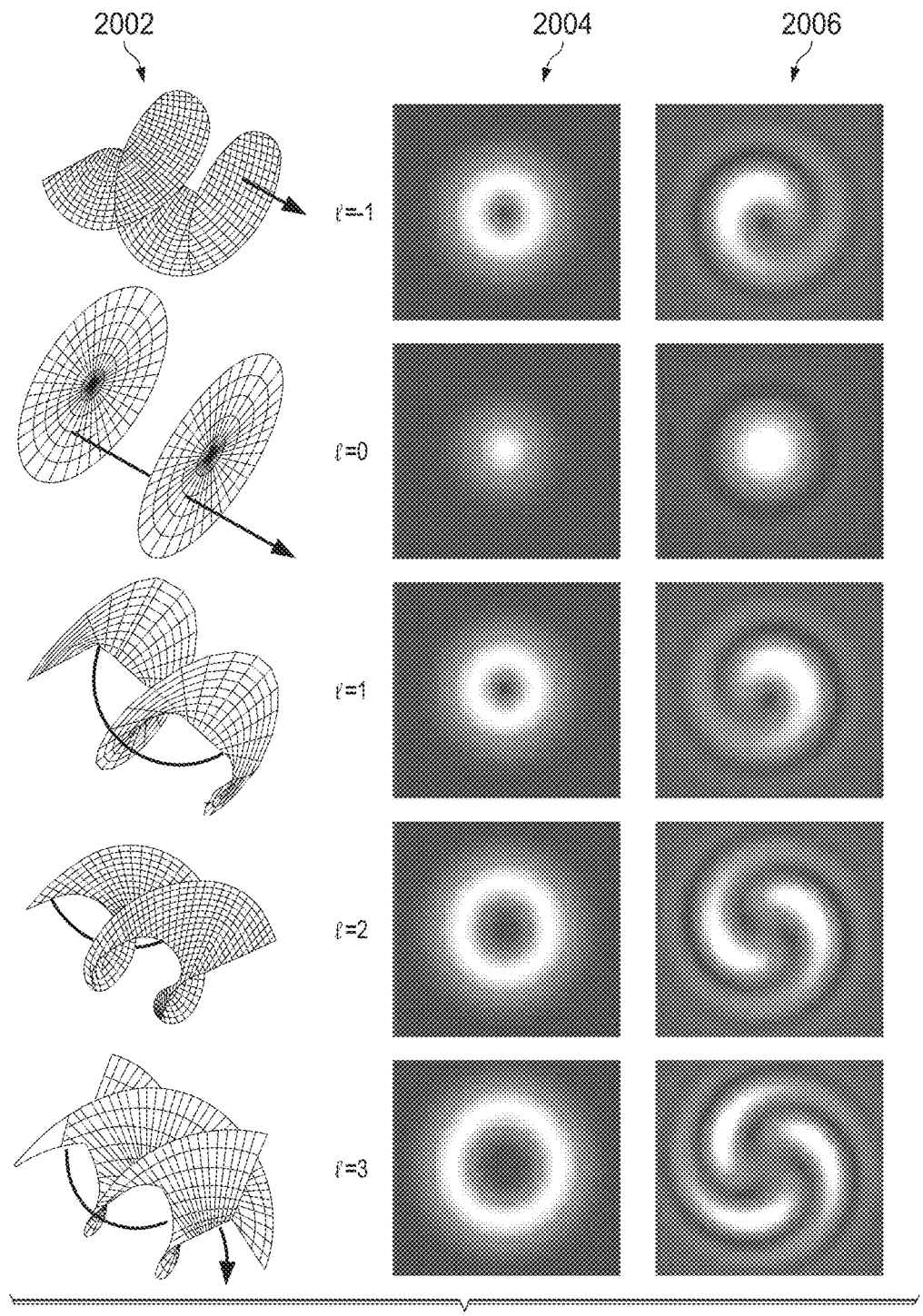
FIG. 20 illustrates the manner in which the output of the OAM generator may be varied by applying different orbital angular momentums thereto.

Referring now to FIG. 20, there is illustrated the manner in which the output of the OAM generator 1206 may vary a signal by applying different orbital angular momentums thereto. FIG. 20 illustrates helical phase fronts in which the Poynting vector is no longer parallel to the beam axis and thus has an orbital angular momentum applied thereto. In any fixed radius within the beam, the Poynting vector follows a spiral trajectory around the axis. Rows are labeled by l, the orbital angular momentum quantum number, $L=l\hbar$ is the beams orbital angular momentum per photon within the output signal. For each l, the left column 2002 is the light beam's instantaneous phase. The center column 2004 comprises the angular intensity profiles and the right column 2006 illustrates what occurs when such a beam interferes with a plane wave and produces a spiral intensity pattern. This is illustrated for orbital angular momentums of −1, 0, 1, 2 and 3 within the various rows of FIG. 23.

Figure 21:
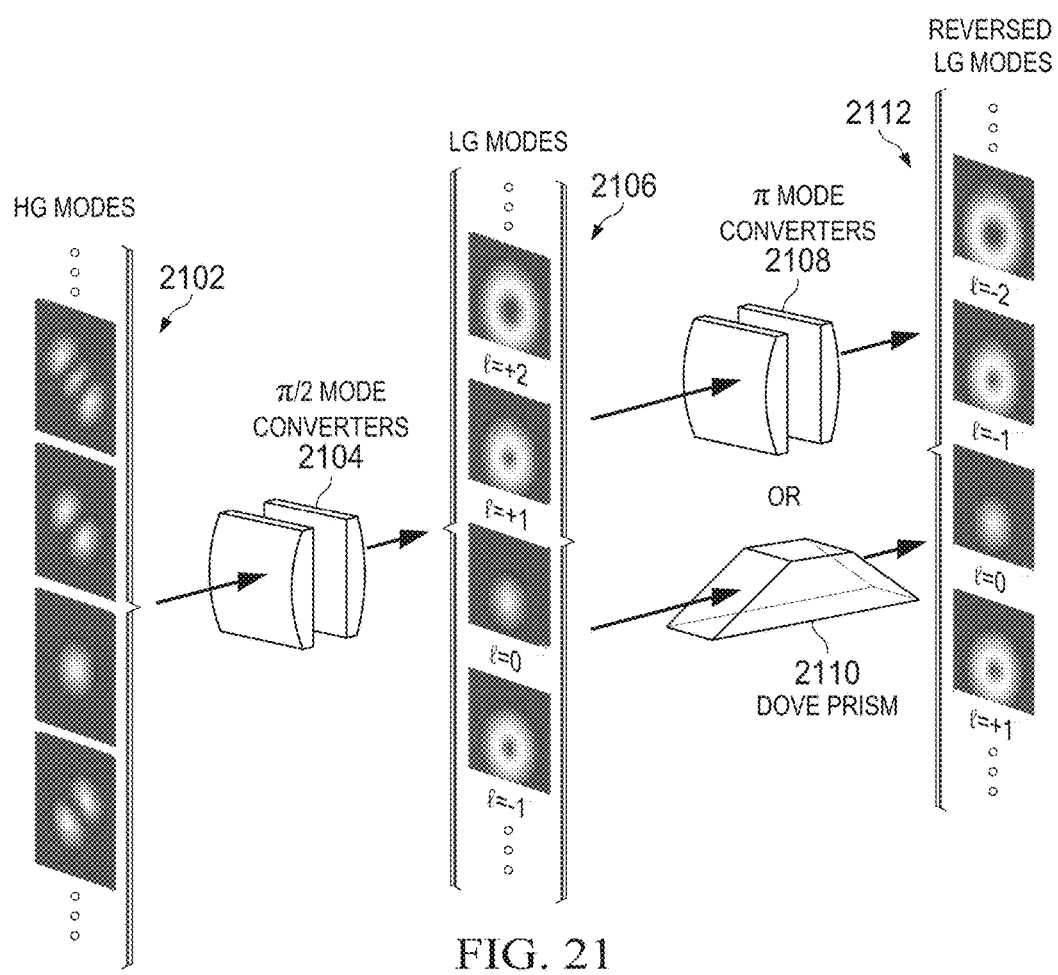
FIG. 21 illustrates an alternative manner in which the OAM generator may convert a Hermite-Gaussian beam to a Laguerre-Gaussian beam.

Referring now to FIG. 21, there is illustrated an alternative manner in which the OAM generator 1206 may convert a Hermite-Gaussian beam output from an emitter 1202 to a Laguerre-Gaussian beams having imparted therein an orbital angular momentum using mode converters 2104 and a Dove prism 2110. The Hermite-Gaussian mode plane waves 2102 are provided to a π/2 mode convertor 2104. The π/2 mode convertor 2104 produce beams in the Laguerre-Gaussian modes 2106. The Laguerre-Gaussian modes beams 2106 are applied to either a π mode convertor 2108 or a dove prism 2110 that reverses the mode to create a reverse Laguerre-Gaussian mode signal 2112.

Figure 22:
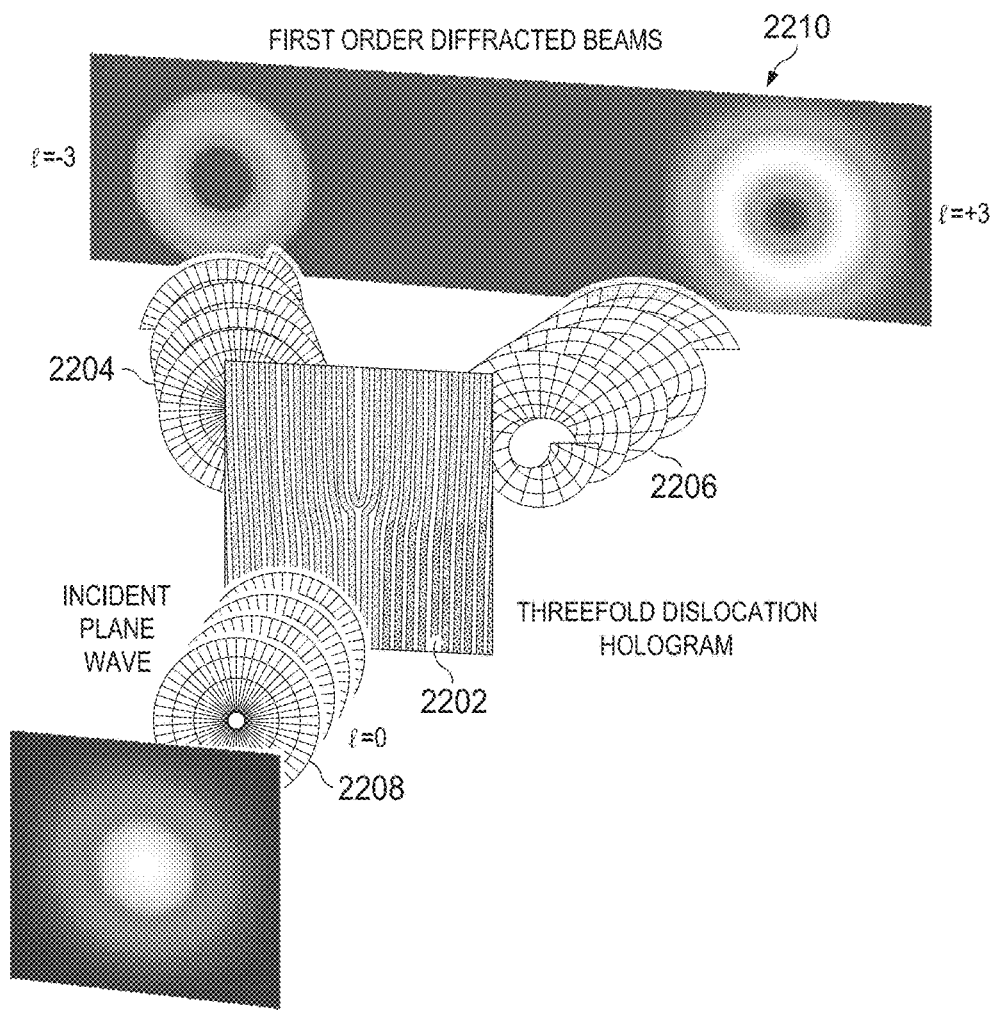
FIG. 22 illustrates the manner in which holograms within an OAM generator may twist a beam of light.

Referring now to FIG. 22, there is illustrated the manner in which holograms within the OAM generator 1206 generate a twisted light beam. A hologram 2202 can produce light beam 2204 and light beam 2206 having helical wave fronts and associated orbital angular momentum lh per photon. The appropriate hologram 2202 can be calculated or generated from the interference pattern between the desired beam form 2204, 2206 and a plane wave 2208. The resulting holographic pattern within the hologram 2202 resembles a diffraction grating, but has a 1-pronged dislocation at the beam axis. When the hologram is illuminated with the plane wave 2208, the first-order diffracted beams 2204 and 2206 have the desired helical wave fronts to provide the desired first ordered diffracted beam display 2210.

Figure 23:
FIG. 23 illustrates the manner in which a sample receives an OAM twisted wave and provides an output wave having a particular OAM signature.

Referring now to FIG. 23, there is more particularly illustrated the manner in which the sample 1210 receives the input OAM twisted wave 1208 provided from the OAM generator 1206 and provides an output OAM wave 1212 having a particular OAM signature associated therewith that depends upon the material or the concentration of a particular monitored material within the sample 1210. The sample 1210 may comprise any sample that is under study and may be in a solid form, liquid form or gas form. The sample material 1210 that may be detected using the system described herein may comprise a variety of different materials. As stated previously, the material may comprise liquids such as blood, water, oil or chemicals. The various types of carbon bondings such as C—H, C—O, C—P, C—S or C—N may be provided for detection. The system may also detect various types of bondings between carbon atoms such as a single bond (methane or Isooctane), dual bond items (butadiene and benzene) or triple bond carbon items such as acetylene.

The sample 1210 may include detectable items such as organic compounds including carbohydrates, lipids (cylcerol and fatty acids), nucleic acids (C, H, O, N, P) (RNA and DNA) or various types of proteins such as polyour of amino $NH_2$ and carboxyl COOH or aminos such as tryptophan, tyrosine and phenylalanine. Various chains within the samples 1210 may also be detected such as monomers, isomers and polymers. Enzymes such as ATP and ADP within the samples may be detected. Substances produced or released by glands of the body may be in the sample and detected. These include items released by the exocrine glands via tube/ducts, endocrine glands released directly into blood samples or hormones. Various types of glands that may have their secretions detected within a sample 1210 include the hypothalamus, pineal and pituitary glands, the parathyroid and thyroid and thymus, the adrenal and pancreas glands of the torso and the hormones released by the ovaries or testes of a male or female.

The sample 1210 may also be used for detecting various types of biochemical markers within the blood and urine of an individual such as melanocytes and keratinocytes. The sample 1210 may include various parts of the body to detect defense substances therein. For example, with respect to the skin, the sample 1210 may be used to detect carotenoids, vitamins, enzymes, b-carotene and lycopene. With respect to the eye pigment, the melanin/eumelanin, dihydroxyindole or carboxylic may be detected. The system may also detect various types of materials within the body's biosynthetic pathways within the sample 1210 including hemoglobin, myoglobin, cytochromes, and porphyrin molecules such as protoporphyrin, coporphyrin, uroporphyrin and nematoporphyrin. The sample 1210 may also contain various bacterial to be detected such as propion bacterium, acnes. Also various types of dental plaque bacteria may be detected such as porphyromonos gingivitis, prevotella intremedi and pre-votella nigrescens. The sample 1210 may also be used for the detection of glucose in insulin within a blood sample 1210. The sample 1210 may also include amyloid-beta detection. Detection of amyloid-beta within the sample may then be used for determinations of early onset Alzheimer's. Higher levels of amyloid-beta may provide an indication of the early stages of Alzheimer's. The sample 1210 may comprise any material that is desired to be detected that provides a unique OAM twist to a signal passing through the sample.

Figure 24:
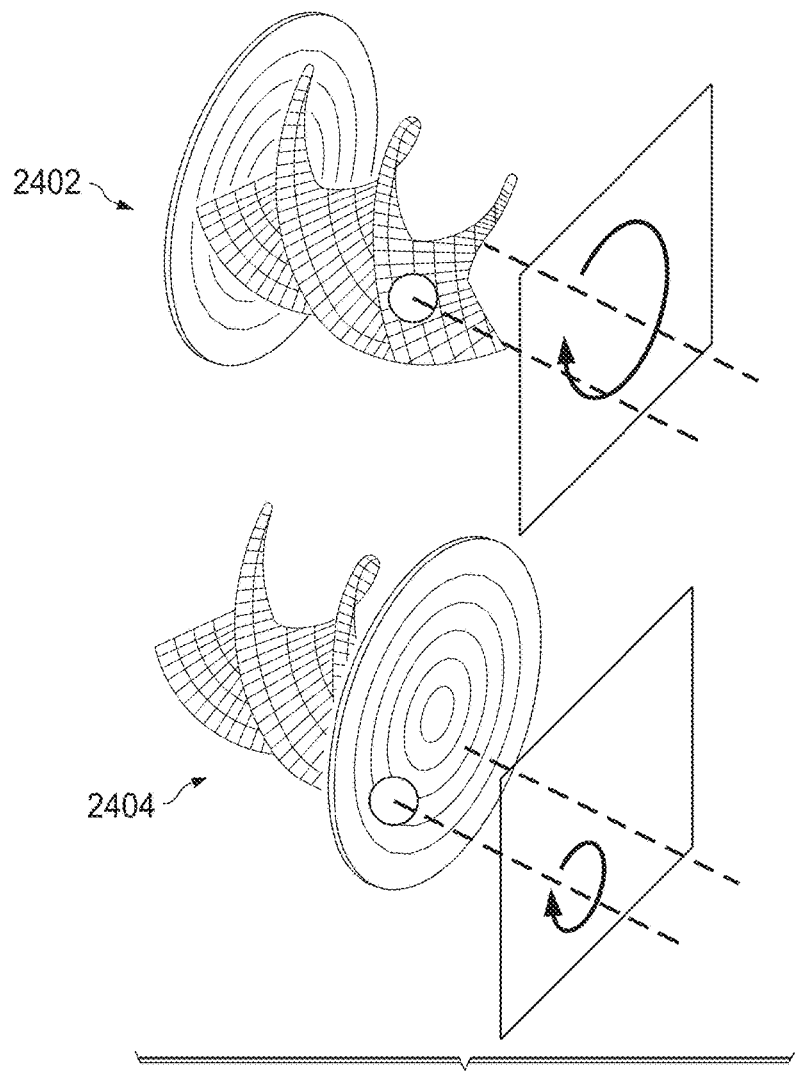
FIG. 24 illustrates the manner in which orbital angular momentum interacts with a molecule around its beam axis.

The orbital angular momentum within the beams provided within the sample 1210 may be transferred from light to matter molecules depending upon the rotation of the matter molecules. When a circularly polarized laser beam with a helical wave front traps a molecule in an angular ring of light around the beam axis, one can observe the transfer of both orbital and spin angular momentum. The trapping is a form of optical tweezing accomplished without mechanical constraints by the ring's intensity gradient. The orbital angular momentum transferred to the molecule makes it orbit around the beam axis as illustrated at 2402 of FIG. 24. The spin angular momentum sets the molecule spinning on its own axis as illustrated at 2404.

The output OAM wave 1212 from the sample 1210 will have an orbital angular momentum associated therewith that is different from the orbital angular momentum provided on the input OAM wave 1208. The difference in the output OAM wave 1212 will depend upon the material contained within the sample 1210 and the concentration of these materials within the sample 1210. Differing materials of differing concentration will have unique orbital angular momentums associated therewith. Thus, by analyzing the particular orbital angular momentum signature associated with the output OAM wave 1212, determinations may be made as to the materials present within the sample 1210 and the concentration of these materials within the sample may also be determined.

Figure 25:
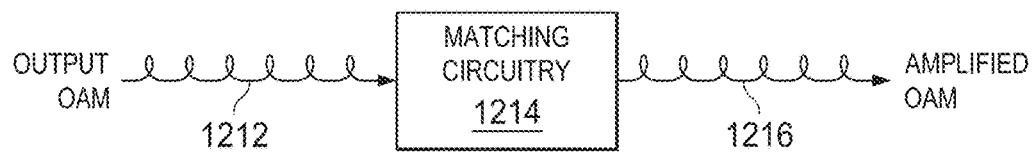
FIG. 25 illustrates a block diagram of the matching circuitry for amplifying a received orbital angular momentum signal.

Referring now to FIG. 25, the matching module 1214 receives the output orbital angular momentum wave 1212 from the sample 1210 that has a particular signature associated therewith based upon the orbital angular momentum imparted to the waves passing through the sample 1210. The matching module 1214 amplifies the particular orbital angular momentum of interest in order to provide an amplified wave having the desired orbital angular momentum of interest 1216 amplified. The matching module 1214 may comprise a matching aperture that amplifies the detection orbital angular momentum associated with a specific material or characteristic that is under study. The matching module 1214 may in one embodiment comprise a holographic filter such as that described with respect to FIGS. 15A-15D in order to amplify the desired orbital angular momentum wave of interest. The matching module 1214 is established based upon a specific material of interest that is trying to be detected by the system. The matching module 1214 may comprise a fixed module using holograms as illustrated in FIGS. 15A-15D or a tunable module in a manner similar to that discussed with respect to the OAM generation module 1206. In this case, a number of different orbital angular momentums could be amplified by the matching module in order to detect differing materials or differing concentrations of materials within the sample 1210. Other examples of components for the matching module 1214 include the use of quantum dots, nanomaterials or metamaterials in order to amplify any desired orbital angular momentum values within a received wave form from the sample 1210.

Figure 26:
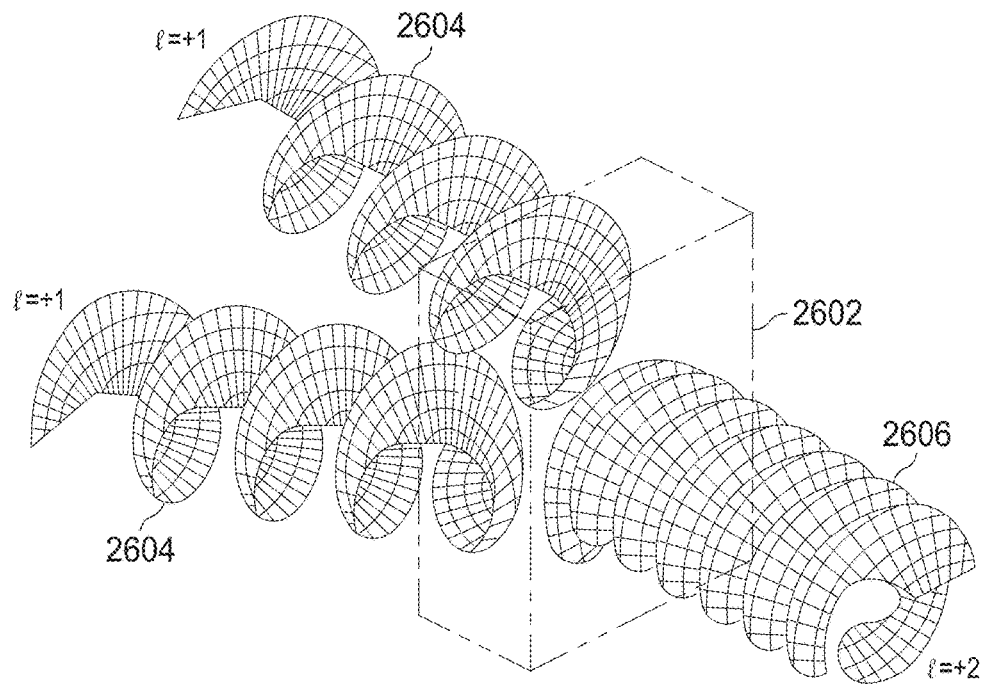
FIG. 26 illustrates the manner in which the matching module may use non-linear crystals in order to generate a higher order orbital angular momentum light beam.

Referring now to FIG. 26, the matching module 1214 rather than using holographic images in order to amplify the desired orbital angular momentum signals may use non-linear crystals in order to generate higher orbital angular momentum light beams. Using a non-linear crystal 2602, a first harmonic orbital angular momentum beam 2604 may be applied to a non-linear crystal 2602. The non-linear crystal 2602 will create a second order harmonic signal 2606.

Figure 27:
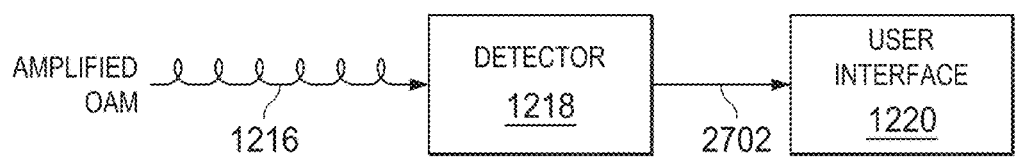
FIG. 27 illustrates a block diagram of an orbital angular momentum detector and user interface.

Referring now to FIG. 27, there is more particularly illustrated the detector 1218 to which the amplified orbital angular momentum wave 1216 from the matching circuit 1214 in order that the detector 1218 may extract desired OAM measurements 2602. The detector 1218 receives the amplified OAM waves 1216 and detects and measures observable changes within the orbital angular momentum of the emitted waves due to the presence of a particular material and the concentration of a particular material under study within the sample 1210. The detector 1218 is able to measure observable changes within the emitted amplified OAM wave 1216 from the state of the input OAM wave 1208 applied to the sample 1210. The extracted OAM measurements 2702 are applied to the user interface 1220. The manner in which the detector 1218 may detect differences within the orbital angular momentum is more particularly illustrates with respect to FIG. 28-30.

Figure 28:
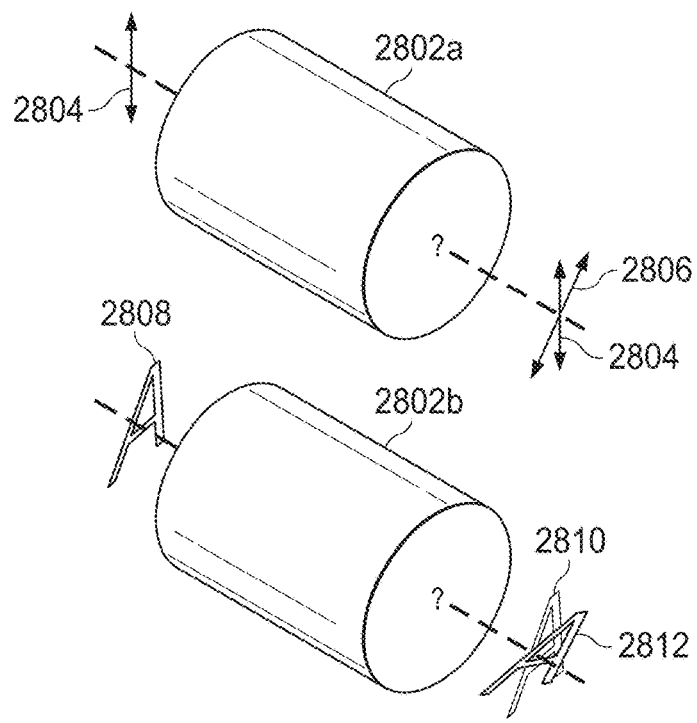
FIG. 28 illustrates the effect of sample concentrations upon the spin angular polarization and orbital angular polarization of a light beam passing through a sample.

FIG. 28 illustrates the difference in impact between spin angular polarization and orbital angular polarization due to passing of a beam of light through a sample 2802. In sample 2802a, there is illustrated the manner in which spin angular polarization is altered responsive to a beam passing through the sample 2802a. The polarization of a wave having a particular spin angular momentum 2804 passing through the sample 2802a will rotate from a position 2804 to a new position 2806. The rotation occurs within the same plane of polarization. In a similar manner, as illustrated with respect to sample 2802b, an image appears as illustrated generally at 2808 before it passes through the sample 2802b. Upon passing the image through the sample 2802b the image will rotate from the position illustrated at 2810 to a rotated position illustrated at 2812. The amount of rotation is dependent upon the presence of the material being detected and the level of concentration of the material being detected within the sample 2802. Thus, as can be seen with respect to the sample 2802 of FIG. 28, both the spin angular polarization and the orbital angular momentum will change based upon the presence and concentration of materials within the sample 2802. By measuring the amount of rotation of the image caused by the change in orbital angular momentum, the presence and concentration of a particular material may be determined.

Figure 29:
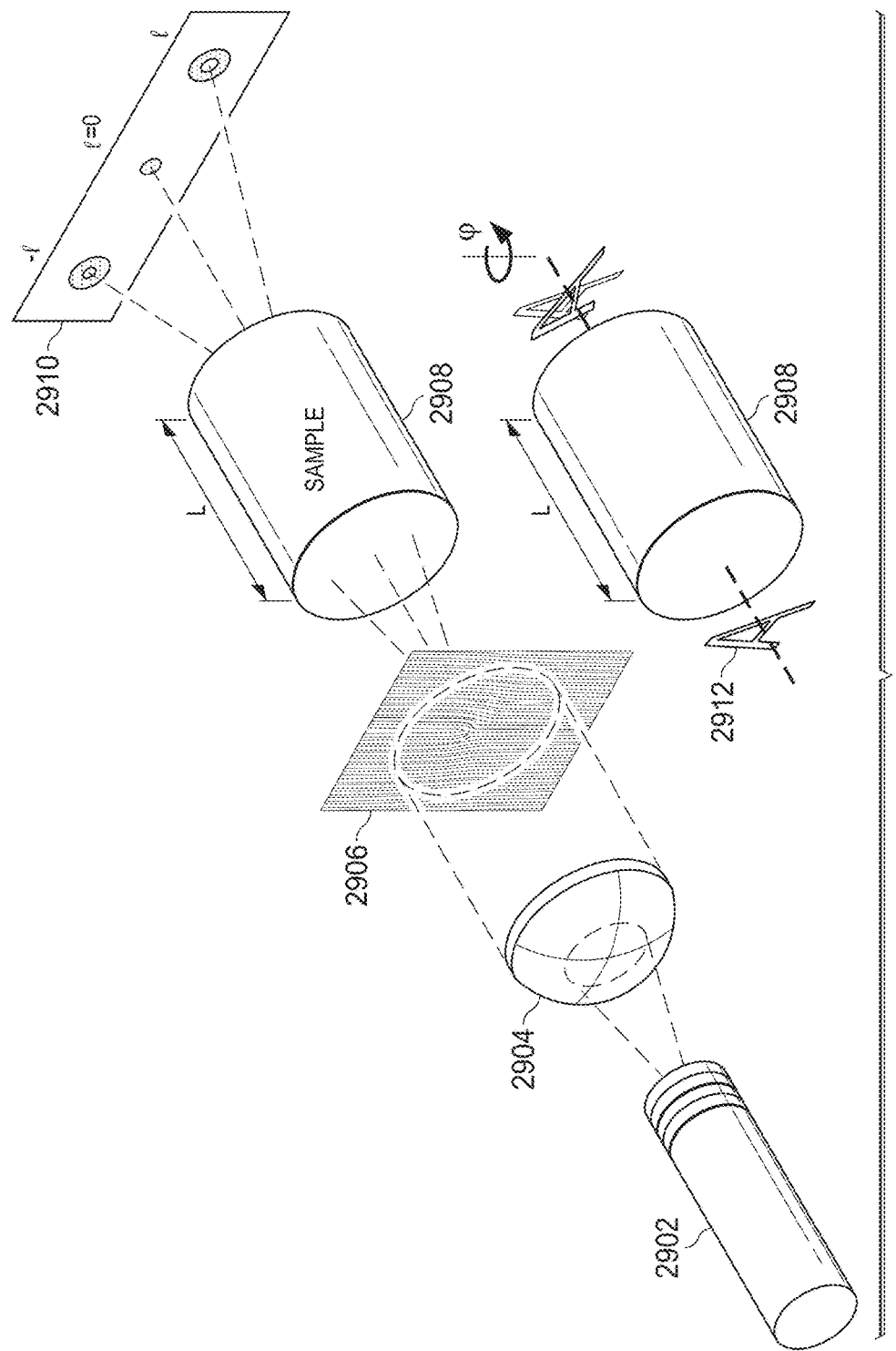
FIG. 29 more particularly illustrates the process that alters the orbital angular momentum polarization of a light beam passing through a sample.

This overall process can be more particularly illustrated in FIG. 29. A light source 2902 shines a light beam through expanding optics 2904. The expanded light beam is applied through a metalab generated hologram 2906 that imparts an orbital angular momentum to the beam. The twisted beam from the hologram 2906 is shined through a sample 2908 having a particular length L. As mentioned previously, the sample 2908 may be located in a container or in its naturally occurring state. This causes the generation of a twisted beam on the output side of the sample 2908 to create a number of detectable waves having various orbital angular momentums 2910 associated therewith. The image 2912 associated with the light beam that is applied to sample 2908 will rotate an angle φ depending upon the presence and concentration of the material within the sample 2908. The rotation φ of the image 2912 is different for each value orbital angular momentum $-l$ or $+l$. The change in rotation of the image $\Delta\varphi$ may be described according to the equation:

$$\Delta\varphi = \varphi_1 - \varphi_{-1} = f(l, L, C)$$

Where l is orbital angular momentum number, L is the path length of the sample and C is the concentration of the material being detected.

Thus, since the length of the sample L is known and the orbital angular momentum may be determined using the process described herein, these two pieces of information may be able to calculate a concentration of the material within the provided sample.

Figure 30:
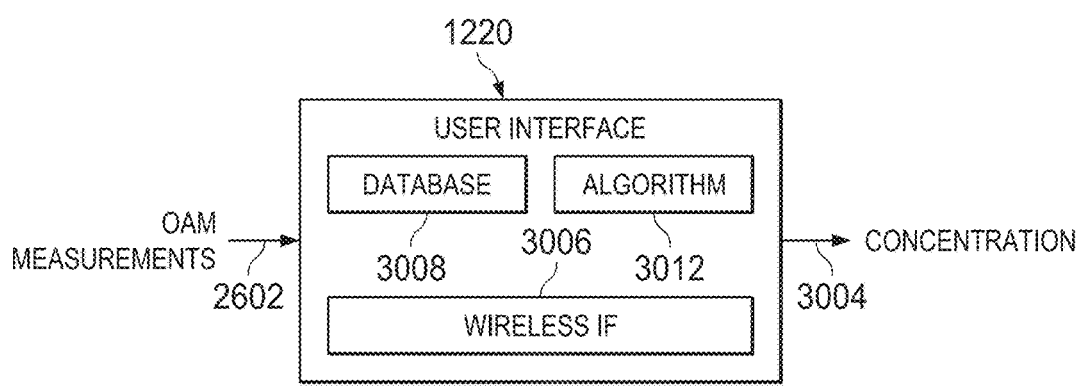
FIG. 30 provides a block diagram of a user interface of the system of FIG. 12.

The above equation may be utilized within the user interface more particularly illustrated in FIG. 30. The user interface 1220 processes the OAM measurements 3002 using an internal algorithm 3002 that provides for the generation of material and/or concentration information 3004 that may be displayed in some type of user display. The algorithm would in one embodiment utilize that equation described herein above in order to determine the material and/or concentration based upon the length of a sample and the detected variation in orbital angular momentum. The process for calculating the material and/or concentration may be done in a laboratory setting where the information is transmitted wirelessly to the lab or the user interface can be associated with a wearable device connected to a meter or cell phone running an application on the cell phone connected via a local area network or wide area network to a personal or public cloud. The user interface 3020 of the device can either have a wired or wireless connection utilizing Bluetooth, ZigBee or other wireless protocols.

Figure 31:
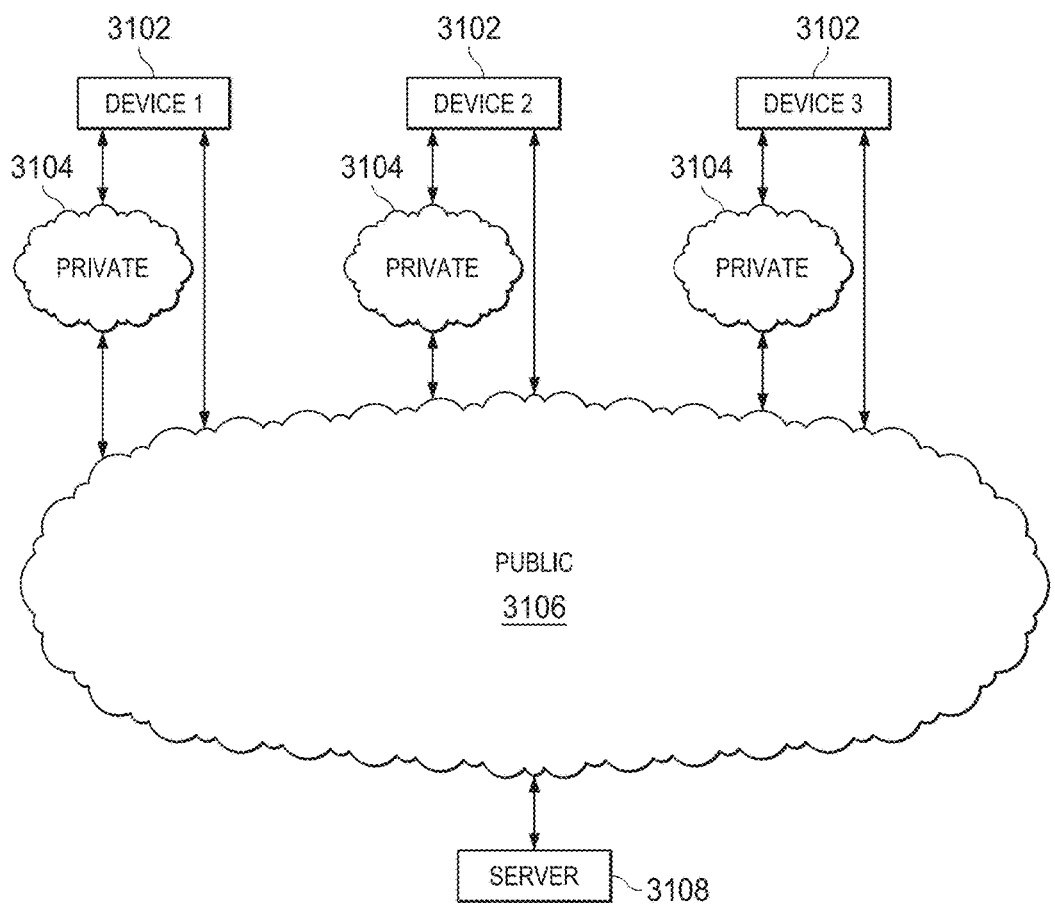
FIG. 31 illustrates a network configuration for passing around data collected via devices such as that illustrated in FIG. 15.

Referring now to FIG. 31, there is illustrated the manner in which the various data accumulated within the user interface 1220 that has been collected in the manner described herein above may be stored and utilized for higher level analysis. Various devices 3102 for collecting data as described herein above may communicate via private network clouds 3104 or with a public cloud 3106. When communicating with a private cloud 3104, the devices 3102 merely store information that is associated with a particular user device that is for use with respect to analysis of the user associated with that user device. Thus, an individual user could be monitoring and storing information with respect to their present glucose concentrations in order to monitor and maintain their diabetes.

Alternatively, when information is compiled from multiple devices 3102 within the public cloud 3106, this information may be provided directly to the public cloud 3106 from the individual devices 3102 or through the private clouds 3104 of the associated network devices 3102. Utilizing this information within the public cloud 3106 large databases may be established within servers 3108 associated with the public cloud 3106 to enable large scale analysis of various health related issues associated with the information processed from each of the individual devices 3102. This information may be used for analyzing public health issues.

Thus, the user interface 1220 in addition to including the algorithm 3002 for determining material and/or concentration information 3004 will include a wireless interface 3006 enabling the collected information to be wirelessly transmitted over the public or private cloud as described with respect to FIG. 31. Alternatively, the user interface may comprise a storage database 3008 enabling the collected information to be locally stored rather than transmitted wirelessly to a remote location.

Figure 32:
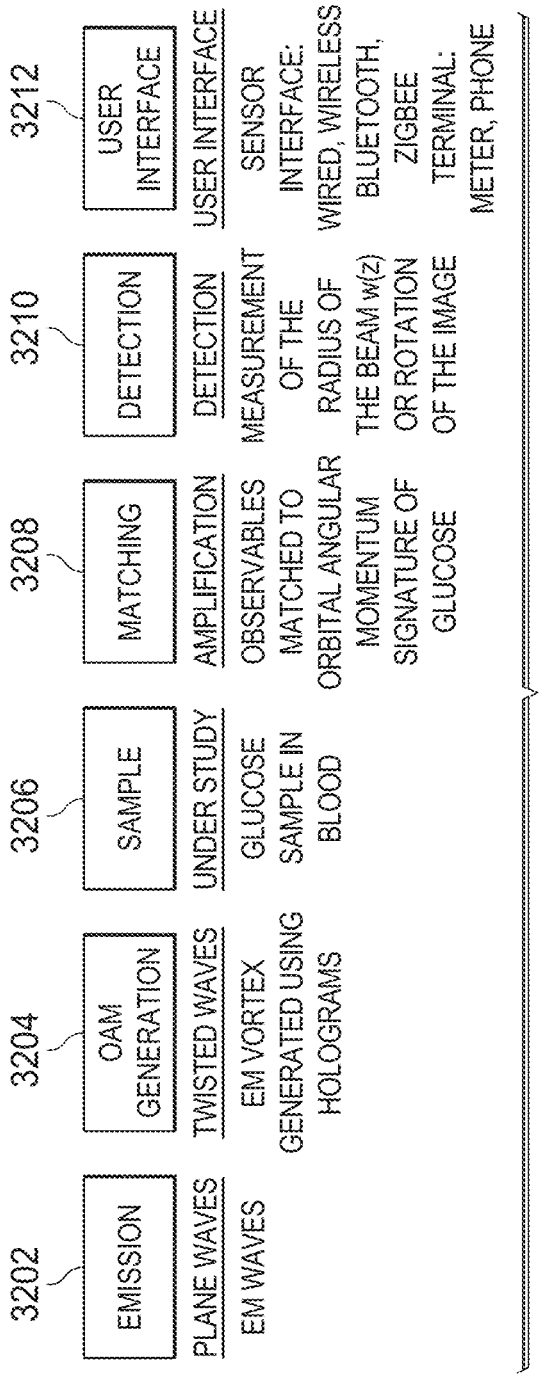
FIG. 32 provides a block diagram of a more particular embodiment of an apparatus for measuring the concentration and presence of glucose using orbital angular momentum.

Referring now to FIG. 32, there is illustrated a particular example of a block diagram of a particular apparatus for measuring the presence an concentration of glucose using the orbital angular momentum of photons of a light beam shined through a glucose sample. While the present example is with respect to the detection of glucose, one skilled in the art would realize that the example would be applicable to the detection of the presence and concentration of any material. The process creates a second-order harmonic with helical light beam using a non-linear crystal such as that described with respect to FIG. 25. The emission module 2402 generates plane electromagnetic waves that are provided to an OAM generation module 3204. The OAM generation module 3204 generates light waves having an orbital angular momentum applied thereto using holograms to create a wave having an electromagnetic vortex. The OAM twisted waves are applied to the sample 3206 that is under study in order to detect the glucose and glucose concentration within a sample. A rotated signature exits the sample 3206 in the manner described previously with respect to FIGS. 28-29 and is provided to the matching module 3208. The matching module 3208 will amplify the orbital angular momentum such that the observed concentrations may be calculated from the orbital momentum of the signature of the glucose. These amplified signals are provided to detection module 3210 which measures the radius of the beam w(z) or the rotation of the image provided to the sample via the light beam. This detected information is provided to the user interface that includes a sensor interface wired or wireless Bluetooth or ZigBee connection to enable the provision of the material to a reading meter or a user phone for the display of concentration information with respect to the sample. In this manner concentrations of various types of material as describe herein may be determined utilizing the orbital angular momentum signatures of the samples under study and the detection of these materials or their concentrations within the sample determine as described.

Provided the orthogonality of Laguerre polynomials, Laguerre Gaussian beams exhibiting orbital angular momentum (OAM) have been determined as a basis for spatial division multiplexing (SDM) in communication applications using for example a mux-demux optical element design. OAM beams are also of interest in quantum informatics. OAM also enables the probing of solutions of chiral and non-chiral molecules.

Figure 33:
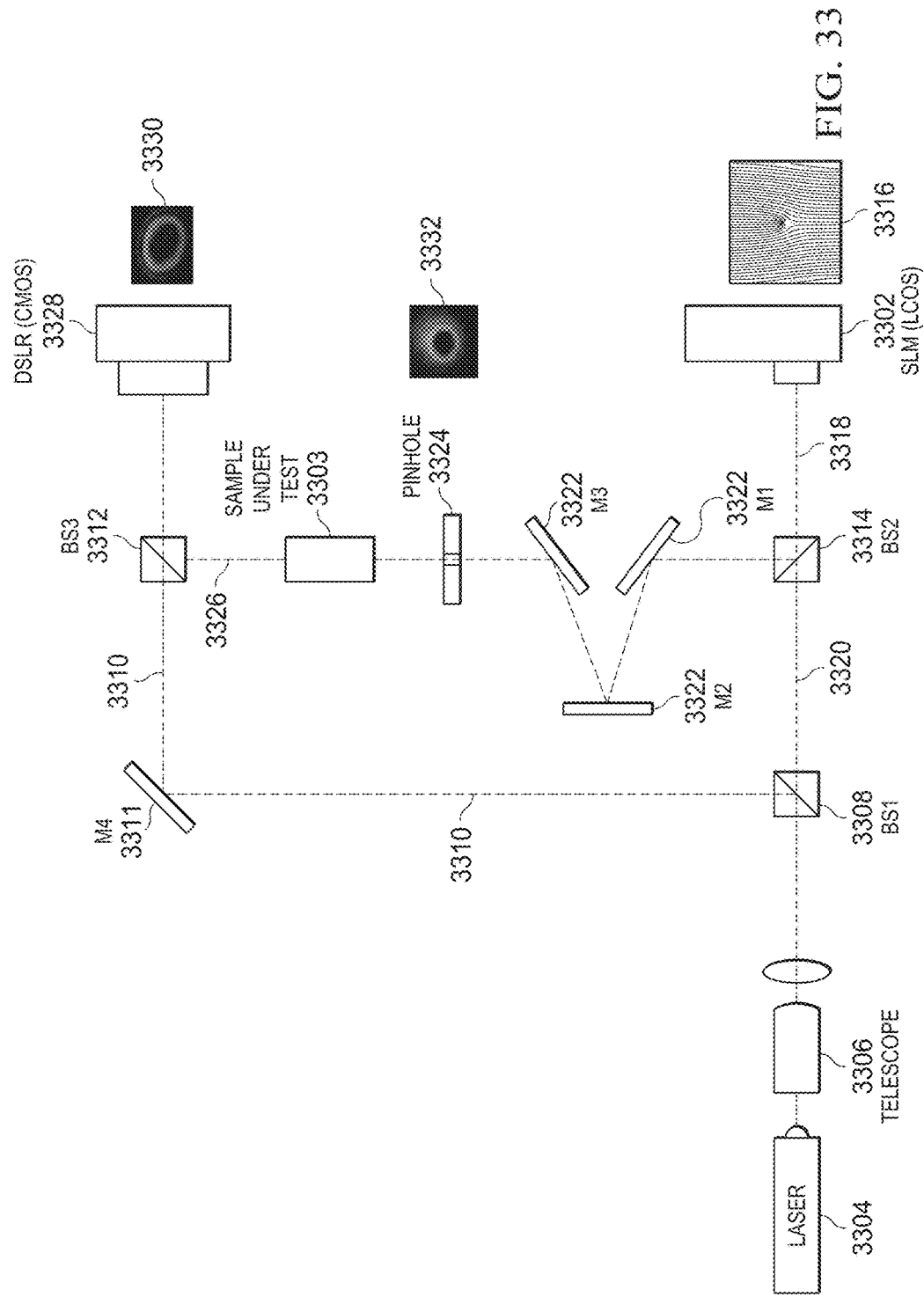
FIG. 33 illustrates an optical system for detecting a unique OAM signature of a signal passing through a sample under test.

FIG. 33 illustrates a further optical configuration for transmitting and detecting information. The twisted nematic LCOS SLM 3302 implements a 1024×768 array with 9 μm pitch and 8-bit resolution covering the visible wavelength range (430-650 nm) and readily interfaced via a VGA connection. A programmable SLM 3302 allows for the generation of a variety of engineered beams. A twisted nematic (TN) liquid crystal on silicon (LCOS) SLM is particularly useful in realizing the holograms that modulate the phase front of the input plane wave 102 (FIG. 1) or Gaussian beam. An SLM is computer addressable using common software packages such as Matlab or Mathematica to define an arbitrary two-dimensional phase shift imprinted onto the beam input using, for example, a hologram.

A collimated input beam is reflected off of a display appropriately encoded by a phase retarding forked gratings, or hologram. The generating equation for the forked gratings may be written as a Fourier series:

$$T(r, \varphi) = \sum_{m=-\infty}^{\infty} t_m \exp\left[-im\left(\frac{2\pi}{D} r\cos\varphi - \ell\varphi\right)\right]$$

Where r and φ are the coordinates, l is the order of the vorticity and D is the period of the rectilinear grating far from the forked pole. The weights, $t_m$, of the Fourier components of the phase grating may be written in terms of Bessel functions of integer order:

$$t_m = (-i)^m J_m(k\beta) \exp(ik\alpha).$$

Where kα and kβ bias and modulate the phase of the forked grating, respectively. Typically only a handful of terms of this series are needed to generate the OAM beams. For example, success has been had with the transfer pattern:

$$T(r, \varphi) = \frac{1}{2} - \frac{1}{2}\sin\left(\frac{2\pi}{D} r\cos\varphi - l\varphi\right)$$

Referring now back to FIG. 33, there is illustrated the optical configuration for detecting a unique signature of a signal passing through a sample under test 3303. The sample 3303 may be in a container or in its naturally occurring state. At a high-level, the instrument comprises a Mach Zehnder interferometer. One arm of the interferometer propagates a reference beam 3310. The reference beam 3310 is created by a laser 3304 generating a light beam including a plurality of plane waves that is transmitted through a telescope 3306. The plane wave light beam from the telescope 3306 passes through a first beam splitter 3308. The beam splitter 3308 generates the reference beam 3310 that is reflected from a mirror 3311 to an interfering circuit 3312. The reference beam 3310 may be a plane wave or, with the addition of a lens, a spherical wavefront may be implemented. This arm is blocked for amplitude only measurements.

In a second arm, the split plane wave beam from the beam splitter 3308 is combined at a beam combiner 3314 with the beam provided from the spatial light modulator 3302. The spatial light modulator 3302 provides a light beam including the forked hologram 3316. The beam combiner 3314 combines the forked hologram beam 3318 from the SLM 3302 and a plane wave beam 3320 from the laser 3304 to generate an OAM or other orthogonal function twisted beam of a known signature. This beam is reflected through a series of mirrors 3322 and focused on a pinhole aperture 3324 before passing the beam having the known orbital angular momentum through the sample under test 3303.

The sample twisted beam 3326 has been interfered at the signal combiner 3312 with the reference beam 3310. This interfered image may then be recorded by a camera or recording device 3328. This provides a unique OAM signature 3330 that may be analyzed in order to detect materials within the sample under test 3303. As can be seen, the unique OAM signature 3330 is different from the signature 3332 of the transmitted beam. The manner in which the signature is altered will be more fully described herein below.

In the second arm, the LCOS SLM 3302 is used to transform a collimated plane wave input beam 3320 into an OAM encoded beam. The SLM 3302 is driven by a Matlab programs on an extended laptop display to provide a display of a forked hologram of any l or ρ. Following the SLM 3302, the beam is reflected through three mirrors 3322 to provide a sufficient distance for the separation of the diffracted OAM modes such that a pinhole iris aperture 3324 may select the desired mode to pass through a sample under test 3303.

Several materials of interest may be detected with OAM signatures using the setup of FIG. 33. Examples of these materials include acetone, isopropyl alcohol, sucrose, amyloid-beta, and glucose in steam distilled water. Spectroscopic grade soda lime glass cuvettes (1 cm×2.5 cm×3 cm) or larger custom-made circular cuvettes having BK7 cover glass in caps may be utilized for containing the sample under test 3303.

The sample under test 3303 is mounted on a translation stage arranged to allow quick and repeatable positioning in and out of the beam path either by movement of the sample or movement of the beam projection apparatus. Additionally, back reflections from the sample services are monitored carefully and blocked by irises so no spurious, secondary interactions occur. The optical power through samples is low (less than 25 μW) to avoid any refractive index dependent thermal gradients in the solution.

The insertion of wave plates, variable retarders and polarizers before and after the sample under test has not revealed any remarkable results. While glucose is well-known to have a polarimetric response at these wavelengths, the concentration path length product is too small to produce a notable shift in the state of polarization. This suggests that the OAM and glucose is a more pronounced response then polarimetry of the molecule.

Images 3330 of the beam at the output of the instrument are recorded using the high-resolution DSLR camera 3328 that is securely mounted perpendicular to the beam propagation direction and remotely triggered to prevent vibration or shift in the instrument. Measurement of ellipticity is performed using Photoshop and Matlab or similar types of image measuring and processing software or applications.

With this instrument, the change to an OAM state imparted on the input beam by a sample under test 3303 can be quantified in both intensity and phase. A series of experiments has been performed using primarily aqueous glucose solutions. A 15% stock solution was diluted to a variety of desired concentrations. Because the different isomers of the sugar interact with each other before attaining equilibrium, a settling time is required for a new or altered solution. Solutions were allowed to equilibrate overnight (approximately 15 hours), a time much longer than the recommended 2 hours, in a Cuvette that was capped to prevent evaporation.

Figure 34:
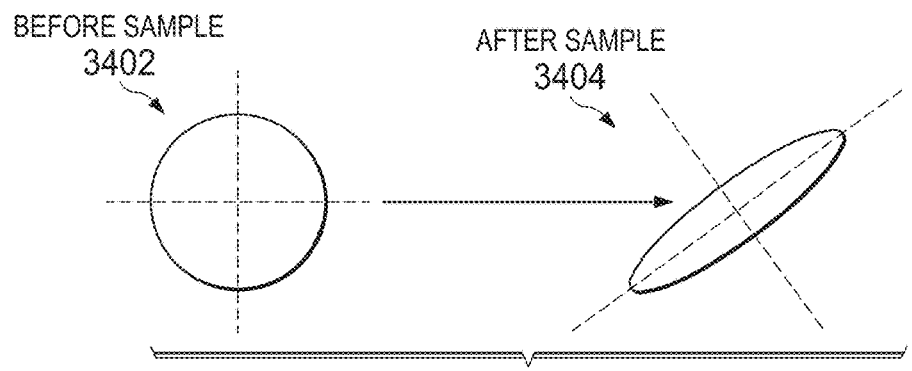
FIG. 34 illustrates the manner in which the ellipticity of an OAM intensity diagram changes after passing through a sample.
Figure 35:
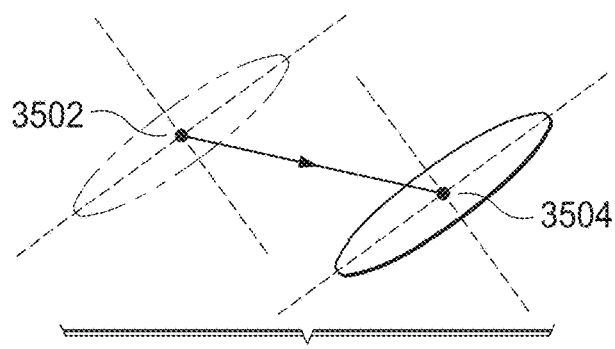
FIG. 35 illustrates the manner in which a center of gravity of an intensity diagram shifts after passing through a sample.
Figure 36:
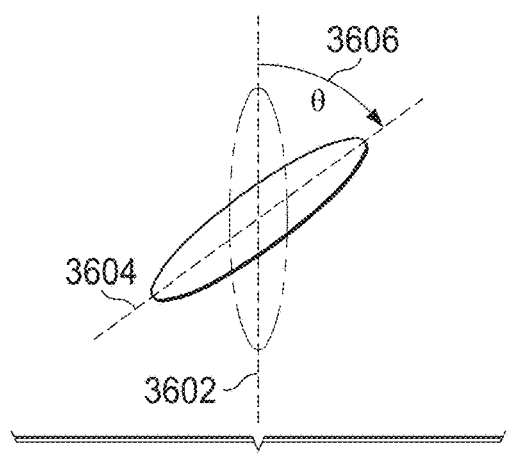
FIG. 36 illustrates the manner in which an axis of the intensity diagram shifts after passing through a sample.

As mentioned previously with respect to FIG. 1, passing through the sample 3303 causes a unique OAM signature to be imparted to the light beam passing through the sample. This unique OAM signature provides an identification of the presence of a material within the sample and of the concentration of the material within the sample. This unique OAM signature includes a number of differences from the OAM signal signature that is input to the sample 3303. The unique OAM signature characteristics are illustrated in FIGS. 34-36. FIG. 34 illustrates the manner in which the ellipticity of the OAM intensity diagram changes after passing through the sample 3303. Initially, as illustrated at 3402, the intensity diagram has a substantially circular shape from the plane wave OAM beam before passing through the sample 3303. After passing through the sample 3303, the intensity diagram has a much more elliptical shape as illustrated generally at 3404. This elliptical shape is a unique characteristic that is different depending upon a material being detected and the concentration of the substance being detected. By detecting the ellipticity of the intensity diagram, a determination may be made of the presence of a particular material within the sample.

FIG. 35 illustrates a further characteristic of the OAM signature that may be altered by passing through a sample 3303. In this case, the center of gravity of the intensity diagram has been shifted. Position 3502 illustrates the initial position of the center of gravity of the intensity diagram before passing through a sample 3303. After passing through the sample 3303, the center of gravity moves to location 3504 that is a noticeable shift from the original position prior to passing through the sample. The shift is uniquely affected by different materials. Thus, the shift in center of gravity may also be used as an OAM distinct signature characteristic with the center of gravity shift indicating the presence of a particular material and the concentration of the material. Based upon an analysis of the shift in the center of gravity of the intensity diagram, a determination of the presence and/or concentration of a material may be made.

A final distinct OAM signature characteristic is illustrated in FIG. 36. In this case, the major axis 3602 of the intensity diagram ellipse shifts from a first position 3602 to a second position 3604 over an angle θ 3606. The major axis of the intensity diagram ellipse rotates from a position 3602 to position 3604 based upon the material being detected. The angle θ is uniquely associated with a particular substance and concentration of the substance being detected. Thus, a material may be detected based upon a determined angle θ within the intensity diagram.

A mathematical model may be used to represent the unique OAM signatures provided by each of changes in eccentricity, shift or translation of the center of gravity in rotation of the axis. The change in eccentricity may be represented by:

$$\text{circle} \Rightarrow x^2 + y^2 + z^2 \Rightarrow \begin{bmatrix} x & y & z \end{bmatrix} \begin{bmatrix} x \\ y \\ z \end{bmatrix}$$

$$\text{3-dimensional ellipse} \Rightarrow \begin{bmatrix} x & y & z \end{bmatrix} \begin{bmatrix} \frac{1}{a^2} & 0 & 0 \\ 0 & \frac{1}{b^2} & 0 \\ 0 & 0 & \frac{1}{c^2} \end{bmatrix} \begin{bmatrix} x \\ y \\ z \end{bmatrix}$$

Where a, b, c are dimensions of the ellipse.

The change in the center of gravity may be represented by a shift or translation in space of a vector v according to the matrix:

$$\text{translation} \Rightarrow \begin{bmatrix} 1 & 0 & v_x \\ 0 & 1 & v_y \\ 0 & 0 & v_z \end{bmatrix}$$

The rotations of the axis may be represented by a series of matrices showing rotations in 3-different orientations:

$$\begin{bmatrix} 1 & 0 & 0 \\ 0 & \cos\alpha & -\sin\alpha \\ 0 & \sin\alpha & \cos\alpha \end{bmatrix} \begin{bmatrix} \cos\beta & 0 & \sin\beta \\ 0 & 1 & 0 \\ -\sin\beta & 0 & \cos\beta \end{bmatrix} \begin{bmatrix} \cos\gamma & -\sin\gamma & 0 \\ \sin\gamma & \cos\gamma & 0 \\ 0 & 0 & 1 \end{bmatrix}$$

Rotation by α  Rotation by β  Rotation by γ

Figure 37A:
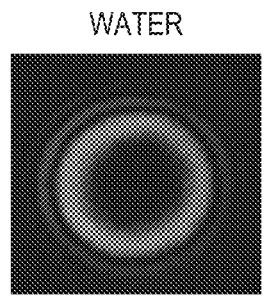
FIG. 37A illustrates an OAM signature of a sample consisting only of water.
Figure 37B:
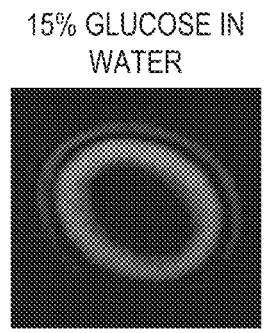
FIG. 37B illustrates an OAM signature of a sample of 15% glucose in water.
Figure 38A:
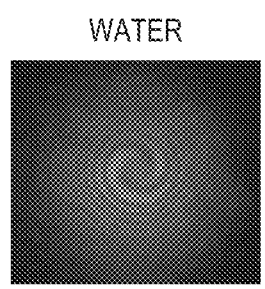
FIG. 38A illustrates an interferogram of a sample consisting only of water.
Figure 38B:
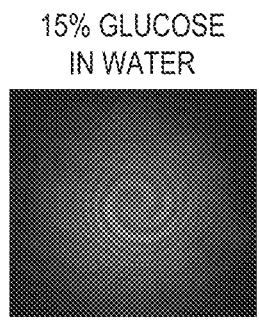
FIG. 38B illustrates an interferogram of a sample of 15% glucose in water.

In an example illustrated in FIGS. 37A and 37B there is shown the application of an OAM beam to a sample consisting only of water (FIG. 37A) and of water including a 15% glucose concentration (FIG. 37B). An l=7 OAM beam at 543 nm is propagated through a 3 cm Cuvette of only water to provide the intensity diagram illustrated in FIG. 37A. The intensity diagram illustrated in FIG. 37B is provided when the l=7 OAM beam passes through a 15% glucose solution in water. The OAM signature manifests itself as an induced ellipticity on the ordinary circular beam amplitude illustrated in the intensity diagram of FIG. 37A. The distinct signature effect may also be observed in phase diagrams such as that illustrated in FIGS. 38A and 38B. FIGS. 38A and 38B illustrate interferograms of an l=2 OAM beam at 633 nm propagating through a 3 cm cuvette of water (FIG. 38A) and a 3 cm cuvette of 15% glucose in water (FIG. 38B). In this particular interferance, the reference beams have the same spherical wave fronts. This is why essentially spiral pattern is observed in the phase measurements. Note in particular, the torsional shift in one of the 2 spirals of the phase front of the sample propagating through the glucose solution. The shift in the spiral pattern is the signature of the interaction in this experiment.

Figure 39:
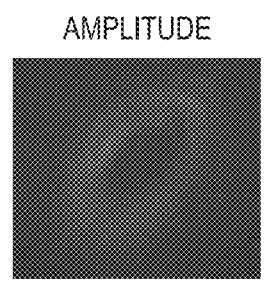
FIG. 39 shows the amplitude of an OAM beam.
Figure 40:
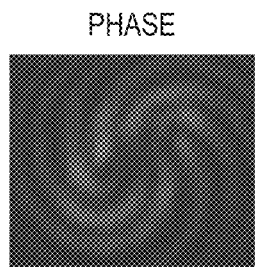
FIG. 40 shows the phase of an OAM beam.

An unperturbed OAM mode propagates through several meters of free space. Glucose samples appear to impart a phase perturbation on an OAM beam causing the OAM mode to topologically be involved in the propagation direction. This effect allows for more sensitive metrology. FIG. 39 shows the amplitude of an OAM beam and FIG. 40 shows the phase of an OAM beam. The beam is an OAM l=beam and is perturbed when passing through a 3 cm Cuvette of a 5% glucose solution and a plane four meters beyond the Cuvette. The ellipticity of the beam is much more pronounced in both amplitude and phase measurements.

Figure 41:
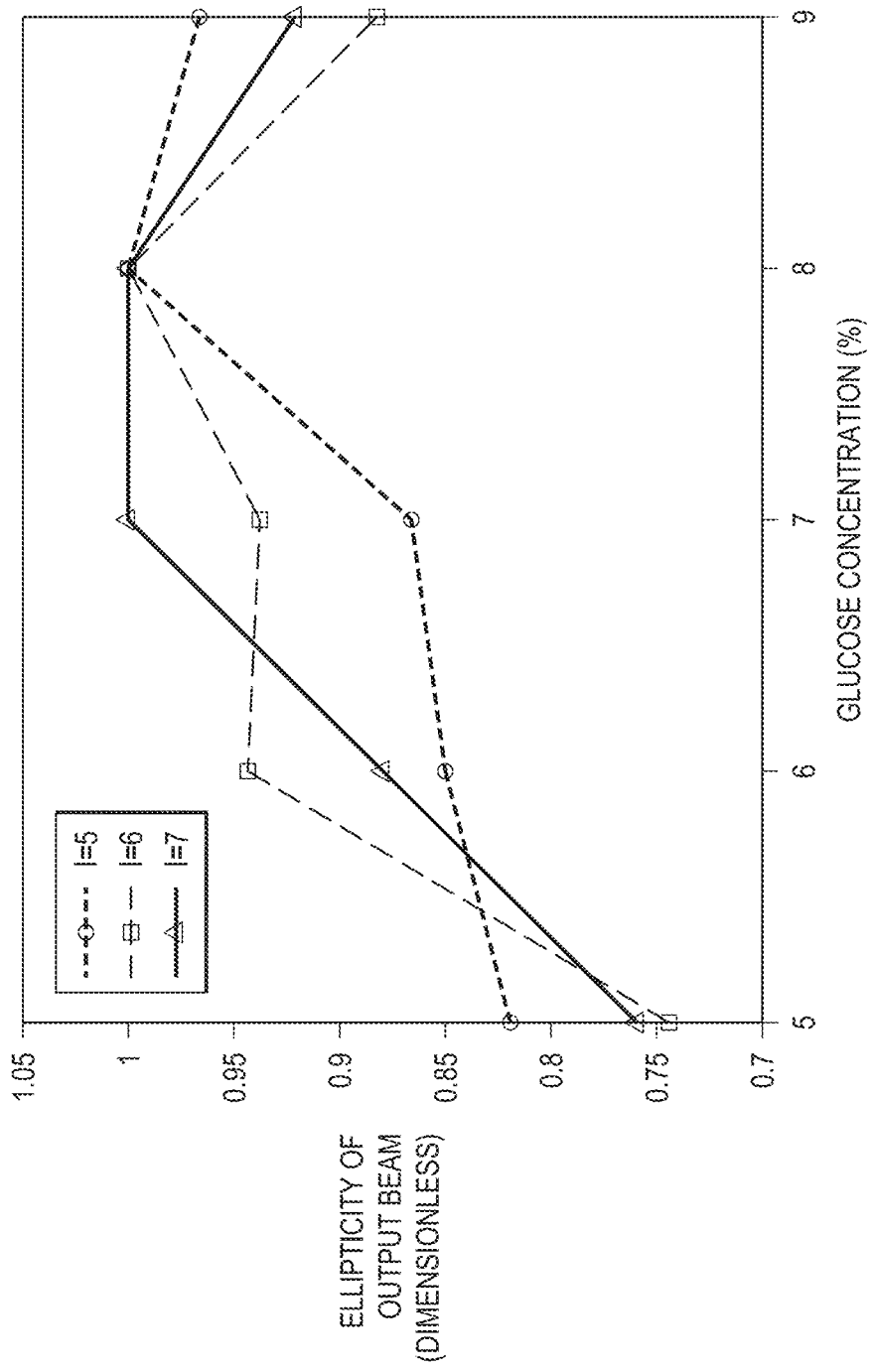
FIG. 41 is a chart illustrating the ellipticity of a beam on the output of a Cuvette for three different OAM modes.

The OAM signature is nonlinear with respect to glucose concentrations and under some conditions, appears to be somewhat periodic with concentration. The ellipticity as a function of glucose concentration is plotted in FIG. 41 using a 3 cm Cuvette, OAM modes l=5, 6, 7, for concentrations of glucose between 5% and 9% in water. Though the preliminary data is noisy, the trend persists over several OAM modes.

There is a broad absorption band for glucose centered at approximately 750 nm, with a FWHM (Full Width Half Maximum), as understood by a person of skill in the art, of approximately 250 nm. Given that the 543 nm absorbance of glucose is 4 times smaller than that for 633 nm, it is interesting that the formal wavelength provides a stronger OAM response. This suggests the interaction is based on the real part of the susceptibility, $\chi'$, rather than its imaginary part, $\chi''$. We note as well that in a separate polarimetry characterization of glucose, using sample cells as long as 20 cm, we measured a 50% larger specific rotation at 543 nm than at 633 nm. In the OAM work, however, we found no discernable change in the effect with polarization, nor did we observe a change in the state of polarization of the beam through the 3 cm samples. This is in keeping with the previous polarization studies of OAM with chiral molecules.

Figure 42A:
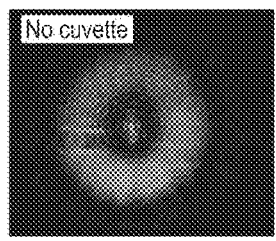
FIGS. 42A-42C illustrates the propagation due to and annulus shaped beam for a Cuvette, water and glucose.
Figure 42B:
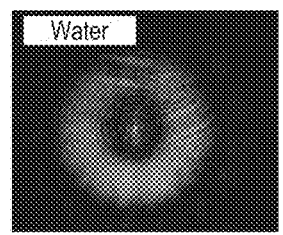
Figure 42C:
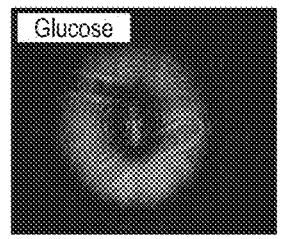

As a check for whether the vorticity of the OAM beam was important for the effect, and annulus was used to project a simple ring of light through a glucose sample. The annulus pattern was printed on a traditional plastic transparency sheet and illuminated with a magnified and collimated 543 nm laser beam. As can be seen in FIGS. 42A-42C, no distortion or signature was observed through Cuvette's of water (FIG. 42B) or Glucose (FIG. 42C) solution. Varying the ring diameter did not change these no results, even for diameters larger than the typical OAM beam. When the annulus diameter was larger than the Cuvette, obvious clipping was observed. The power level of the beams in this test was as much in order of magnitude higher than in the OAM experiments. Thus, any thermal effects would have been accentuated.

Since aqueous solutions of glucose were used in the experiments, the study of propagation of OAM in water is relevant. Steam distilled water, the solvent used in dilution, was placed in clean new cells of the variety of links and cross-sections and propagation of a variety of OAM beams through this medium was measured. No discernible differences were observed among an OAM mode propagated through a dry cell, a sample of path length 0.5 cm and a sample of 8 cm of water.

Figure 43:
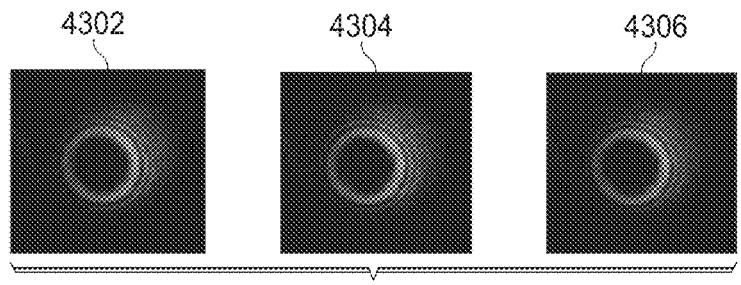
FIG. 43 illustrates OAM propagation through water for differing drive voltages.

Another null result was observed in an experiment were in an OAM beam was propagated through a liquid crystal that variable retarder. In FIG. 43, reference Nos. 4302, 4304 and 4306 show an l=7 OAM mode at the output of a variable wave plate for differing drive voltages between 0.1 V and 6 V.

Figure 44:
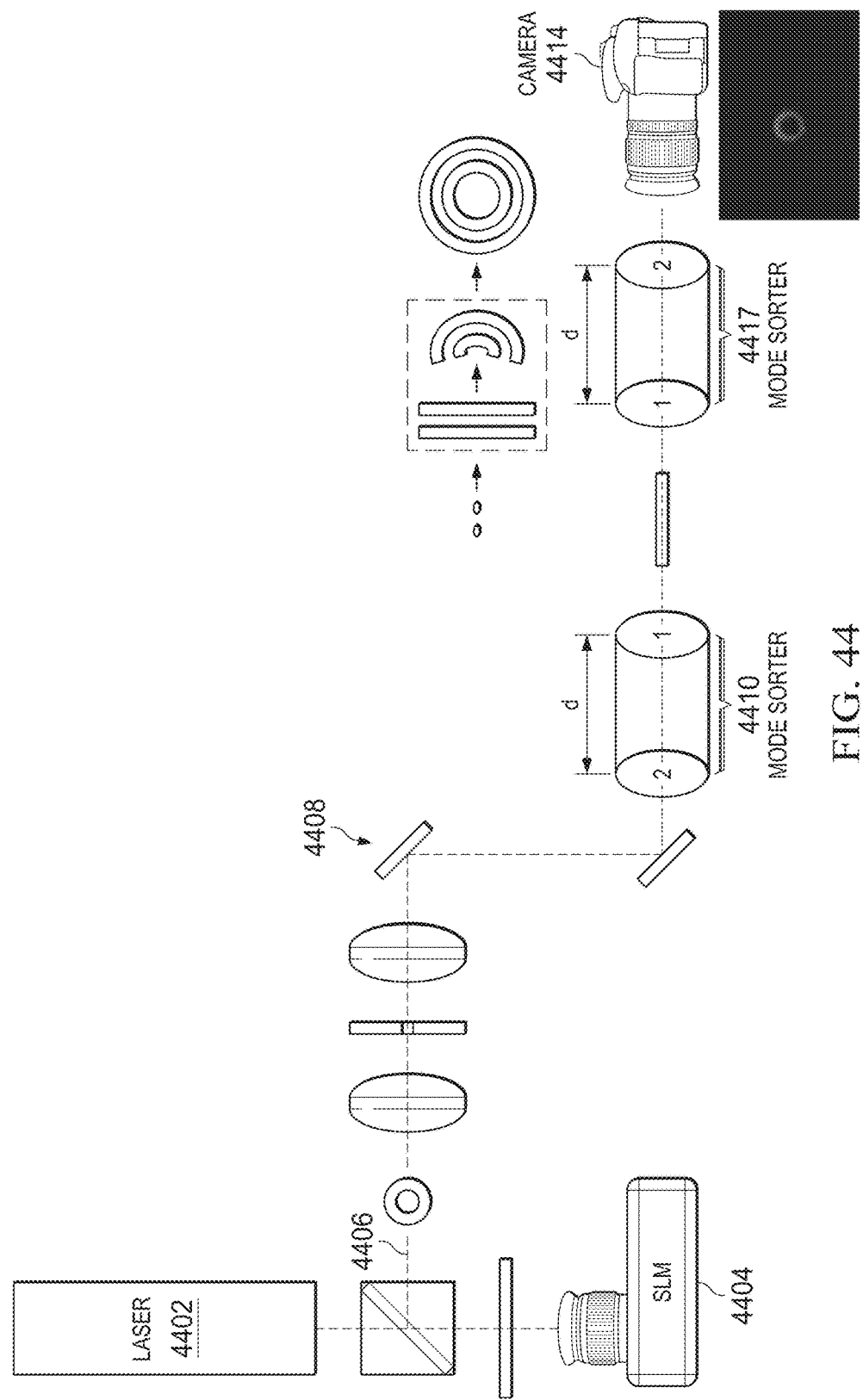
FIG. 44 illustrates an example of a light beam that is altered by a hologram to produce an OAM twisted beam.

It is been noted that the eccentricities of the intensity images produced by shining orthogonal function processed beam through a sample can have variances due to a number of differing factors. FIG. 44 illustrates an example wherein a light beam produced by a laser 4402 is altered by a hologram provided by an SLM 4404 to generate an OAM twisted beam 4406. The OAM twisted beam in addition to being altered by OAM functions may also be processed using Hermite Gaussian functions, Laguerre Gaussian functions or any other type of orthogonal function. The OAM twisted beam is focused through a system 4408 of lenses and mirrors to direct the beam through a mode sorter 4410. The beam is separated into its different modes when regenerated at mode sorter 4412 and the intensity images may be registered by a camera 4414.

Figure 45:
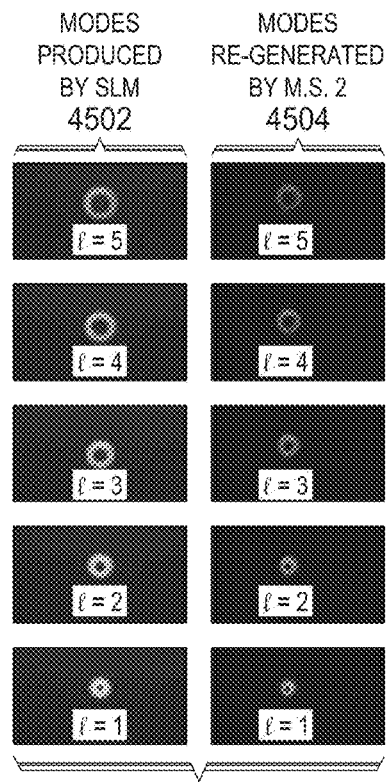
FIG. 45 illustrates various OAM modes produced by a spatial light modulator.

The beam from the laser 4402 has an inherent eccentricity of approximately 0.15. As illustrated in FIG. 45, there are illustrated various OAM modes produced by the SLM in column 4502 for l=5, 4, 3, 2, 1. As can be seen, there are differences between the eccentricity of the modes produced by the SLM, and the eccentricity of the modes regenerated by the second mode sorter 4412.

Figure 46:
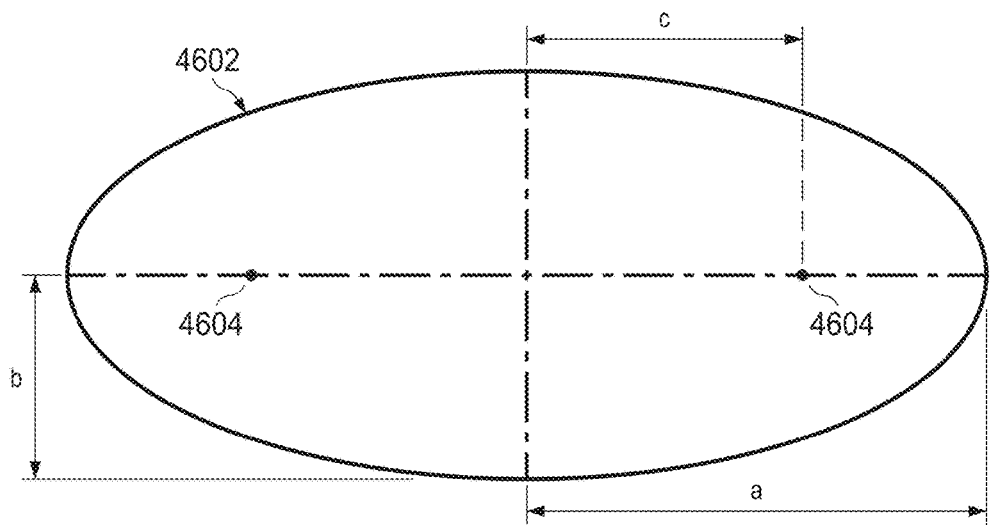
FIG. 46 illustrates an ellipse.

Measurements of eccentricity are performed using Photoshop and Matlab to identify the specific signatures. Referring now to FIG. 46, there is illustrated an example of an ellipse 4602 having a radius "a" along its long axis, a radius "b" along a short axis and a distance "c" to the foci 4604 of the ellipse. The eccentricity of the ellipse is represented by the equation eccentricity=c/a. The eccentricity varies from 0 to 1 with 0 representing a circle and 1 representing a line. The eccentricity equation is calculated according to the following equations:

$$U_{xx} = \frac{1}{N}\sum_{i=1}^{N} x_i^2 + \frac{1}{12}$$

$$U_{yy} = \frac{1}{N}\sum_{i=1}^{N} y_i^2 + \frac{1}{12}$$

$$U_{xy} = \frac{1}{N}\sum_{i=1}^{N} y_i x_i$$

$$\text{common} = \sqrt{(U_{xx} - U_{yy})^2 + 4U_{xy}^2}$$

$$2a = 2\sqrt{2}\sqrt{U_{xx}U_{yy} + \text{common}}$$

$$2b = 2\sqrt{2}\sqrt{U_{xx}U_{yy} - \text{common}}$$

$$c = \sqrt{a^2 - b^2}$$

$$\text{Eccentricity} = \frac{c}{a}$$

where $x_i$ is the x location of the pixels in the ellipse; $y_i$ is the y locations of the pixels in the ellipse; and N is the number of pixels in the ellipse.

It is been found that the eccentricity is greater than 0 when no sample is present within the cuvette. A number of factors contribute to the nonzero eccentricity. OAM twisted signals have been found to provide different eccentricities based upon a number of different factors that may affect the index of refraction. These factors include things such as the sample distribution of the material within the cuvette due to gravity, the distance of the camera from the spatial light modulator and the camera angle of the camera from the spatial light modulator. Other factors affecting the eccentricity are the cuvette positioning, the index of refraction changes do to the sample, the cuvette shape and the beam incidence and exit angle from the cuvette.

Several image processing factors have also been determined not to cause changes that are outside the margin of error. Changes based on software processing errors, a circular mask that is not OAM, the sample sitting time or the sample interaction with the glass or plastic comprising the sample container may provide eccentricity changes, but the changes are not due to optical impairments caused by the cuvette orientation, camera alignment, etc. These factors do produce some changes in eccentricity, but they are within the margin of error and the majority of the eccentricity change is based on the signature of the molecule being detected.

Figure 47:
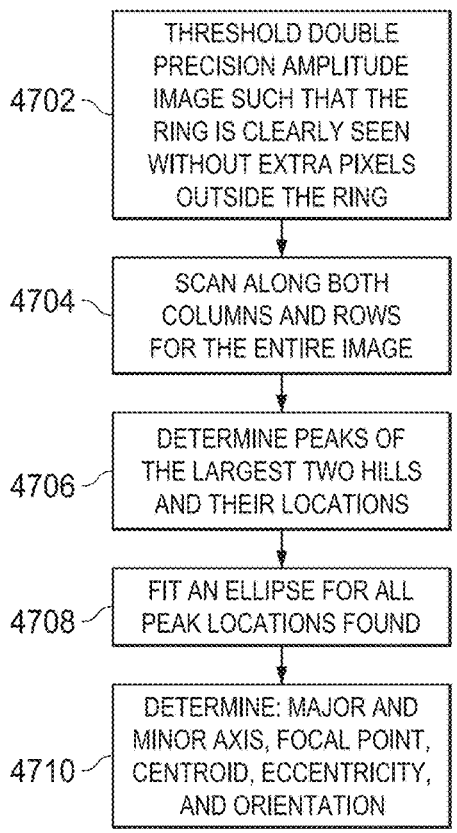
FIG. 47 is a flow diagram illustrating a process for analyzing intensity images.

Referring now to FIG. 47, there is illustrated a flow diagram for analyzing intensity images taken by the camera 4414. The intensity image has applied thereto threshold double precision amplitude to enable the ring to be clearly seen without extra pixels outside of the ring at step 4702. Next at step 4701, both columns and rows are scanned along for the entire image. The peaks of the two largest hills and their locations are determined at step 4706. An ellipse is fit at step 4008 for all peak locations found. Finally, at step 4710, a determination is made of the major and minor axis of the ellipse, the focal point of the ellipse, the centroid, eccentricity and orientation of the ellipse.

Figure 48:
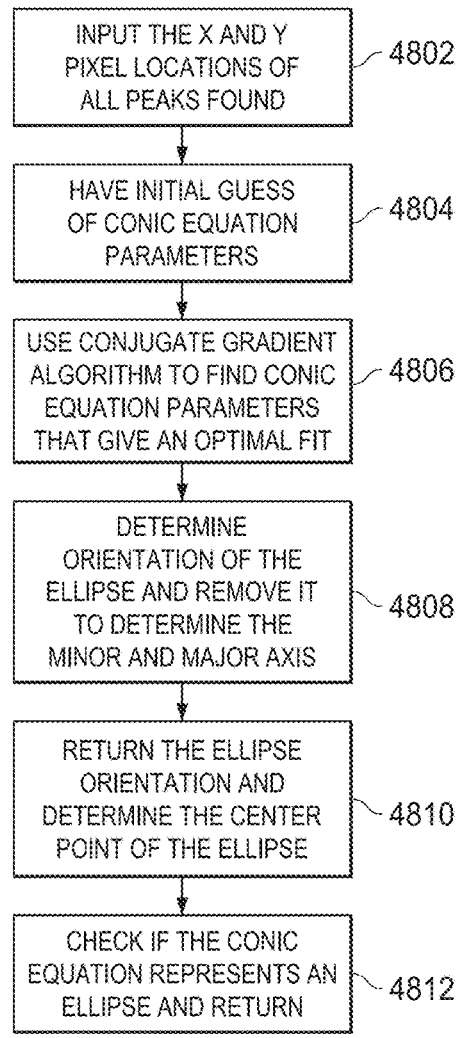
FIG. 48 illustrates an ellipse fitting algorithm.

FIG. 48 illustrates an ellipse fitting algorithm flowchart. The X and Y pixel locations are input at step 4802 for all peaks that are found. An initial guess is provided at step 4804 for the conic equation parameters. The conic equation parameters comprise parameters A, B, C, D and E for the equation $Ax^2+By^2+Cx+Dy+E=0$. The conjugate gradient algorithm is used at step 4806 to find conic equation parameters that provide an optimal fit. An orientation of the ellipse is determined at step 4808 and moved to determine the major and minor axis. The determination of step 4808 is determined according to the equation $$\phi = \frac{1}{2}\tan^{-1}\frac{B}{C-A}$$

The ellipse orientation is returned at step 4810 to determine the central point of the ellipse. Finally, at step 4812, a determination is made if the conic equation represents an ellipse. For an ellipse parameters A and B will exist and have the same sign but will not be equal. Based upon this analysis it is been determined that lateral shift of up to 1 mm can cause significant changes in the measured eccentricity due to clipping of up to 0.2.

It will be appreciated by those skilled in the art having the benefit of this disclosure that this system and method for the detection of the presence of materials within a sample based on a unique signature. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. An apparatus for identifying a material within a sample, comprising:
   signal generation circuitry for generating a first signal including a first orbital angular momentum (OAM) signature and applying the first signal to the sample; and
   a detector for receiving the first signal after the first signal passes through the sample and identifying the material within the sample based on a detected second orbital angular momentum signature caused by an interaction of the first signal with chiral molecules within the sample.

2. The apparatus of claim 1, wherein ambient light scattering by the chiral molecules within the sample is not detected.

3. The apparatus of claim 1, wherein the signal generation circuitry further comprises:
   a plane wave signal generator for generating a signal comprised of a plurality of plane waves; and
   a spatial light modulator for generating the first signal having the first orbital angular momentum signature applied thereto responsive to receipt of the signal comprised of the plurality of plane waves.

4. The apparatus of claim 1, wherein the signal generation circuitry further comprises:
   a plane wave signal generator for generating a signal comprised of a plurality of plane waves; and
   an amplitude mask for generating the first signal having the first orbital angular momentum signature applied thereto responsive to receipt of the signal comprised of the plurality of plane waves.

5. The apparatus of claim 1, wherein the signal generation circuitry further comprises:
   a plane wave signal generator for generating a signal comprised of a plurality of plane waves; and
   a phase mask for generating the first signal having the first orbital angular momentum signature applied thereto responsive to receipt of the signal comprised of the plurality of plane waves.

6. The apparatus of claim 1, wherein the signal generation circuitry further comprises:
   a plane wave signal generator for generating a signal comprised of a plurality of plane waves; and
   a digital light processor for generating the first signal having the first orbital angular momentum signature applied thereto responsive to receipt of the signal comprised of the plurality of plane waves.

7. The apparatus of claim 1, wherein the signal generation circuitry further comprises:
   a plane wave signal generator for generating a signal comprised of a plurality of plane waves; and
   orbital angular momentum generation circuitry for generating the first signal having the first orbital angular momentum signature applied thereto responsive to receipt of the signal comprised of the plurality of plane waves, wherein the orbital angular momentum circuitry further comprises at least one hologram for applying the first orbital angular momentum signature to the signal comprised of the plurality of plane waves.

8. The apparatus of claim 7, wherein the detector further includes circuitry for determining a phase of the first signal after the first signal passes through the sample, wherein the circuitry determines the phase by interfering the first signal having the second orbital angular momentum signature therein with an interference signal having the plane waves therein.

9. The apparatus of claim 1, wherein the detector identifies the material within the sample based on a detected amplitude measurement and phase measurement of the second orbital angular momentum signature caused by an interaction of the first signal with the chiral molecules within the sample.

10. A method for identifying a material within a sample, comprising:
    generating a first signal including a first orbital angular momentum (OAM) signature therein;
    applying the first signal to the sample;
    receiving the first signal after the first signal passes through the sample; and
    identifying the material within the sample based on a detected second orbital angular momentum signature caused by an interaction of the first signal with chiral molecules within the sample.

11. The method of claim 10, wherein ambient light scattering by the chiral molecules within the sample is not detected.

12. The method of claim 10, wherein the step of generating further comprises:
    generating a signal comprised of a plurality of plane waves; and
    generating the first signal having the first orbital angular momentum signature applied thereto responsive to receipt of the signal comprised of the plurality of plane waves using a spatial light modulator.

13. The method of claim 10, wherein the step of generating further comprises:
   generating a signal comprised of a plurality of plane waves; and
   generating the first signal having the first orbital angular momentum signature applied thereto responsive to receipt of the signal comprised of the plurality of plane waves using an amplitude mask.

14. The method of claim 10, wherein the step of generating further comprises:
   generating a signal comprised of a plurality of plane waves; and
   generating the first signal having the first orbital angular momentum signature applied thereto responsive to receipt of the signal comprised of the plurality of plane waves using a phase mask.

15. The method of claim 10, wherein the step of generating further comprises:
   generating a signal comprised of a plurality of plane waves; and
   generating the first signal having the first orbital angular momentum signature applied thereto responsive to receipt of the signal comprised of the plurality of plane waves using a digital light processor.

16. The method of claim 10, wherein the step of generating further comprises:
   generating a signal comprised of a plurality of plane waves; and
   generating the first signal having the first orbital angular momentum signature applied thereto responsive to receipt of the signal comprised of the plurality of plane waves by applying the first orbital angular momentum signature to the signal comprised of the plurality of plane waves.

17. The method of claim 16, wherein the step of identifying further includes:
   determining a phase of the first signal after the first signal passes through the sample; and
   interfering the first signal having the second orbital angular momentum signature therein with an interference signal having the plane waves therein to determine the phase of the first signal after the first signal passes through the sample.

18. The method of claim 10, wherein the step of identifying further comprises:
   detecting an amplitude measurement and phase measurement of the second orbital angular momentum signature caused by an interaction of the first signal with the chiral molecules in the sample; and
   identifying the material within the sample based on the detected amplitude measurement and phase measurement of the second orbital angular momentum signature.

19. A detector for identifying a material within a sample, comprising:
   an input interface for receiving a first signal having an orbital angular momentum (OAM) signature applied thereto caused by passing through the sample;
   detection circuitry for detecting the orbital angular momentum signature within the first signal and identifying the material within the sample based on the detected orbital angular momentum signature caused by an interaction of the first signal with chiral molecules within the sample as the first signal passes through the sample.

20. The detector of claim 19, wherein the detection circuitry identifies the material within the sample based on a detected amplitude measurement and phase measurement of the orbital angular momentum signature caused by an interaction of the first signal with chiral molecules within the sample.

* * * * *